US012629175B2

(12) United States Patent
Davison et al.

(10) Patent No.: US 12,629,175 B2
(45) Date of Patent: May 19, 2026

(54) BONE FIXATION SYSTEM AND DEVICE

(71) Applicant: Forma Medical, Inc., Camp Hill, PA (US)

(72) Inventors: Andrew Charles Davison, Hummelstown, PA (US); James A. Gault, Lincoln, RI (US); Jesse F. Doty, Hixson, TN (US)

(73) Assignee: Forma Medical, Inc., Camp Hill, PA (US)

( * ) Notice: Subject to any disclaimer, the term of this patent is extended or adjusted under 35 U.S.C. 154(b) by 665 days.

(21) Appl. No.: 18/102,429

(22) Filed: Jan. 27, 2023

(65) Prior Publication Data

US 2023/0270466 A1      Aug. 31, 2023

Related U.S. Application Data

(60) Provisional application No. 63/304,108, filed on Jan. 28, 2022.

(51) Int. Cl.
| | |
|---|---|
| *A61B 17/56* | (2006.01) |
| *A61B 17/17* | (2006.01) |
| *A61B 17/84* | (2006.01) |
| *A61B 17/86* | (2006.01) |
| *A61B 17/88* | (2006.01) |
| *A61B 17/90* | (2006.01) |
| *A61B 17/70* | (2006.01) |

(52) U.S. Cl.
CPC .......... *A61B 17/56* (2013.01); *A61B 17/1775* (2016.11); *A61B 17/1782* (2016.11); *A61B 17/864* (2013.01); *A61B 17/8897* (2013.01); *A61B 17/90* (2021.08); *A61B 2017/564* (2013.01); *A61B 17/7035* (2013.01); *A61B 17/848* (2013.01)

(58) Field of Classification Search
CPC . A61B 17/17; A61B 17/1739; A61B 17/1775; A61B 17/1782; A61B 17/56; A61B 2017/564; A61B 17/7291; A61B 17/864; A61B 17/88; A61B 17/8897; A61B 17/90
See application file for complete search history.

(56) References Cited

U.S. PATENT DOCUMENTS

| | | | | |
|---|---|---|---|---|
| 7,901,408 | B2 * | 3/2011 | Ek | A61F 2/4003 |
| | | | | 606/88 |
| 8,034,056 | B2 | 10/2011 | Fencl et al. | |
| 8,080,045 | B2 | 12/2011 | Wooton, III | |
| 8,579,912 | B2 * | 11/2013 | Isaza | A61B 17/1742 |
| | | | | 606/86 R |

(Continued)

FOREIGN PATENT DOCUMENTS

| | | |
|---|---|---|
| WO | 2011008739 A2 | 1/2011 |
| WO | 2018157168 A1 | 8/2018 |
| WO | 2021091071 A1 | 5/2021 |

OTHER PUBLICATIONS

Authorized Officers Natalija Jagodic and Arillo J. Fernandez, International Search Report and the Written Opinion, International Patent Application PCT/US2023/011754, Completed May 23, 2023, 14 pp.

*Primary Examiner* — Larry E Waggle, Jr.
(74) *Attorney, Agent, or Firm* — Offit Kurman, P.A.; Gregory A. Grissett

(57)      ABSTRACT

A bone fixation device configured to fix one or more bone segments is provided.

6 Claims, 36 Drawing Sheets

(56)                    References Cited

U.S. PATENT DOCUMENTS

| | | | |
|---|---|---|---|
| 8,911,446 B2 | 12/2014 | Thornes et al. | |
| 8,979,850 B2 * | 3/2015 | Johnstone | A61B 17/8866 |
| | | | 606/86 R |
| 9,161,793 B2 * | 10/2015 | Huebner | A61B 17/8875 |
| 9,198,676 B2 | 12/2015 | Pilgeram et al. | |
| 10,888,338 B2 | 1/2021 | Lintula et al. | |
| 10,918,400 B2 * | 2/2021 | Wong | A61B 90/39 |
| 10,918,431 B2 | 2/2021 | Barmes et al. | |
| 10,939,945 B2 | 3/2021 | Wang et al. | |
| 10,959,741 B2 | 3/2021 | Dacosta et al. | |
| 10,987,146 B2 | 4/2021 | Denham | |
| 11,000,297 B2 | 5/2021 | Robertson et al. | |
| 11,123,120 B2 | 9/2021 | Dacosta et al. | |
| 11,141,172 B2 | 10/2021 | Laird et al. | |
| 11,179,168 B2 | 11/2021 | Dacosta et al. | |
| 11,213,303 B2 | 1/2022 | Russell et al. | |
| 11,331,112 B2 | 5/2022 | Bettenga | |
| 11,395,691 B2 | 7/2022 | Dacosta et al. | |
| 11,439,412 B2 | 9/2022 | Woodard et al. | |
| 11,504,139 B2 | 11/2022 | Woodard et al. | |
| 2007/0100342 A1 | 5/2007 | Green et al. | |
| 2010/0256639 A1 | 10/2010 | Tyber et al. | |
| 2013/0046313 A1 | 2/2013 | Lian | |
| 2019/0274697 A1 * | 9/2019 | Santangelo | A61B 17/1764 |
| 2021/0052308 A1 | 2/2021 | Thoren et al. | |
| 2021/0259842 A1 * | 8/2021 | Feng | A61B 17/7001 |
| 2021/0386437 A1 | 12/2021 | Dacosta et al. | |
| 2022/0031340 A1 | 2/2022 | Dogue et al. | |
| 2022/0054145 A1 | 2/2022 | Zaima | |
| 2022/0117593 A1 | 4/2022 | Carlo, III et al. | |
| 2022/0192685 A1 | 6/2022 | Gazonnet et al. | |

* cited by examiner

200

210

200

210

200

210

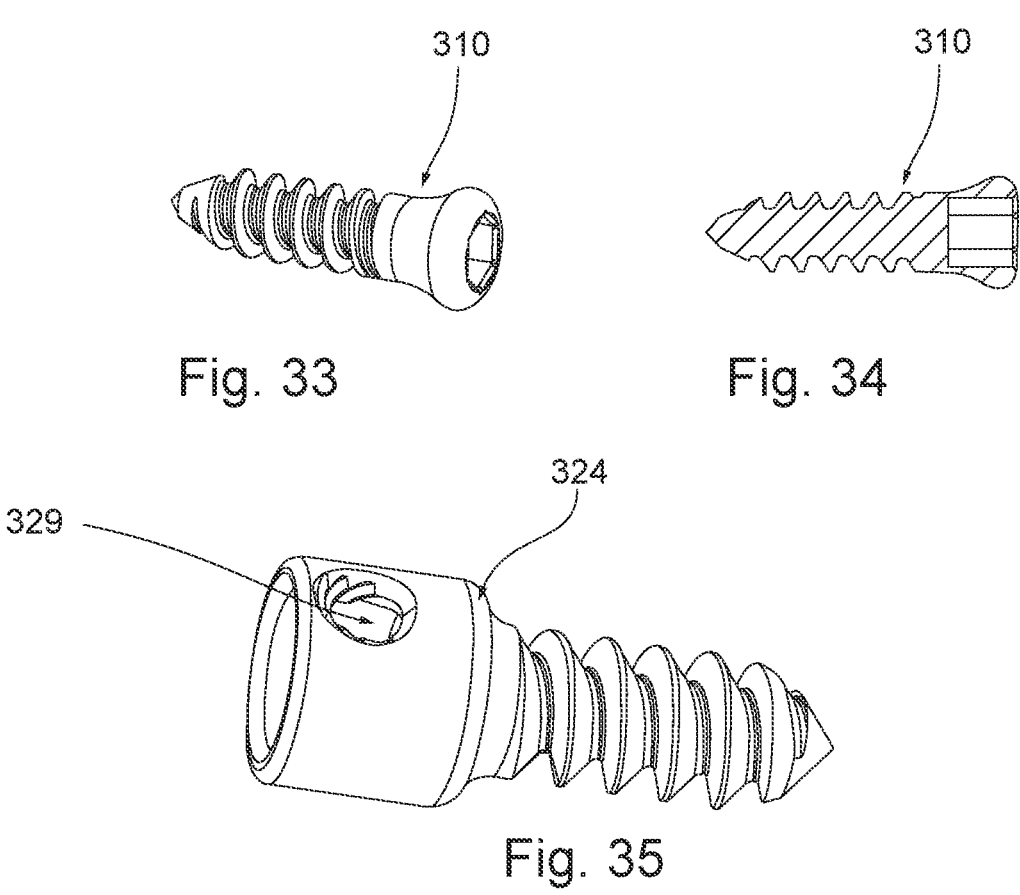
Fig. 33                    Fig. 34
Fig. 35
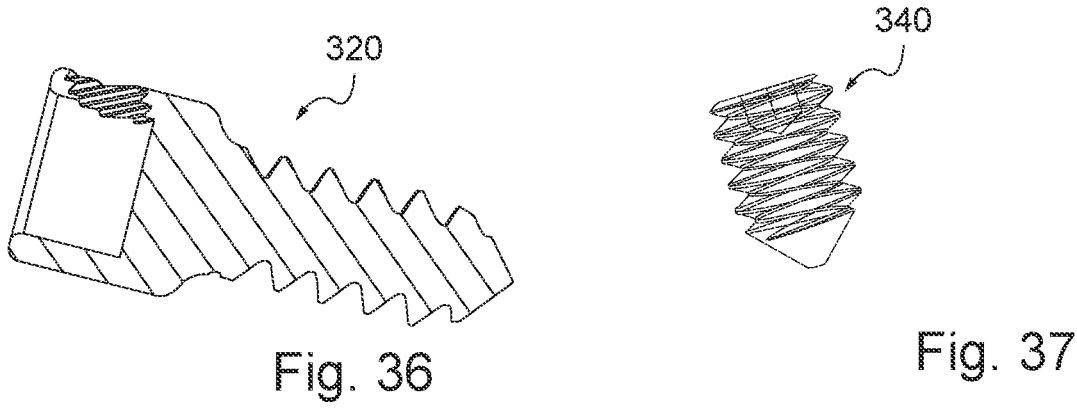
Fig. 36                              Fig. 37

411 410 412 417

411 410 412

410 412

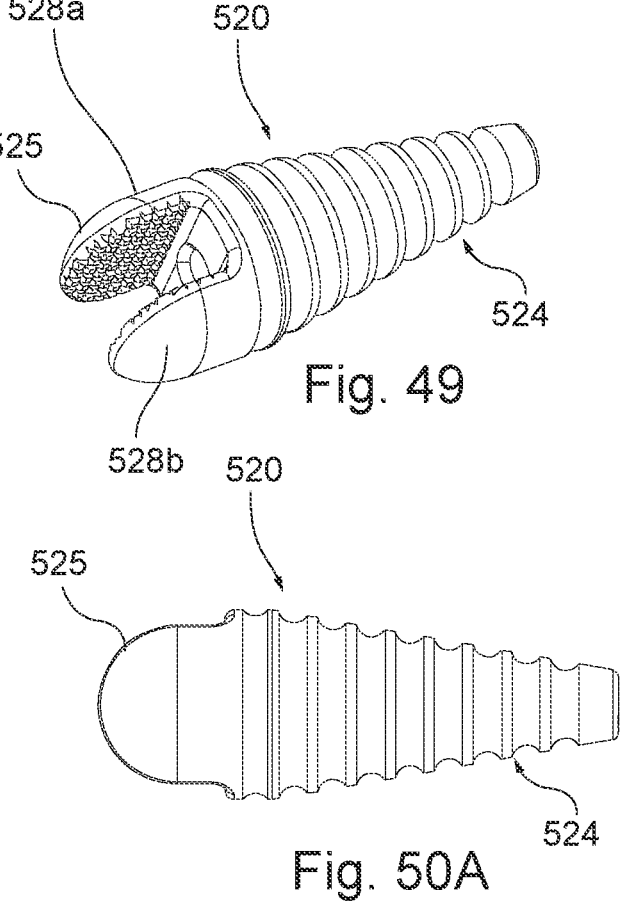
Fig. 49
Fig. 50A
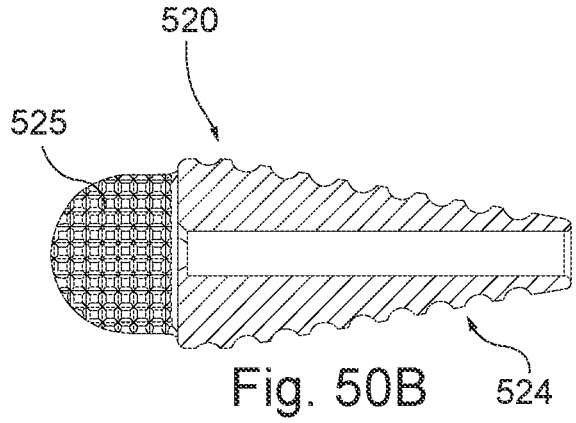
Fig. 50B

800

844

800

848

823

800

844

820

848

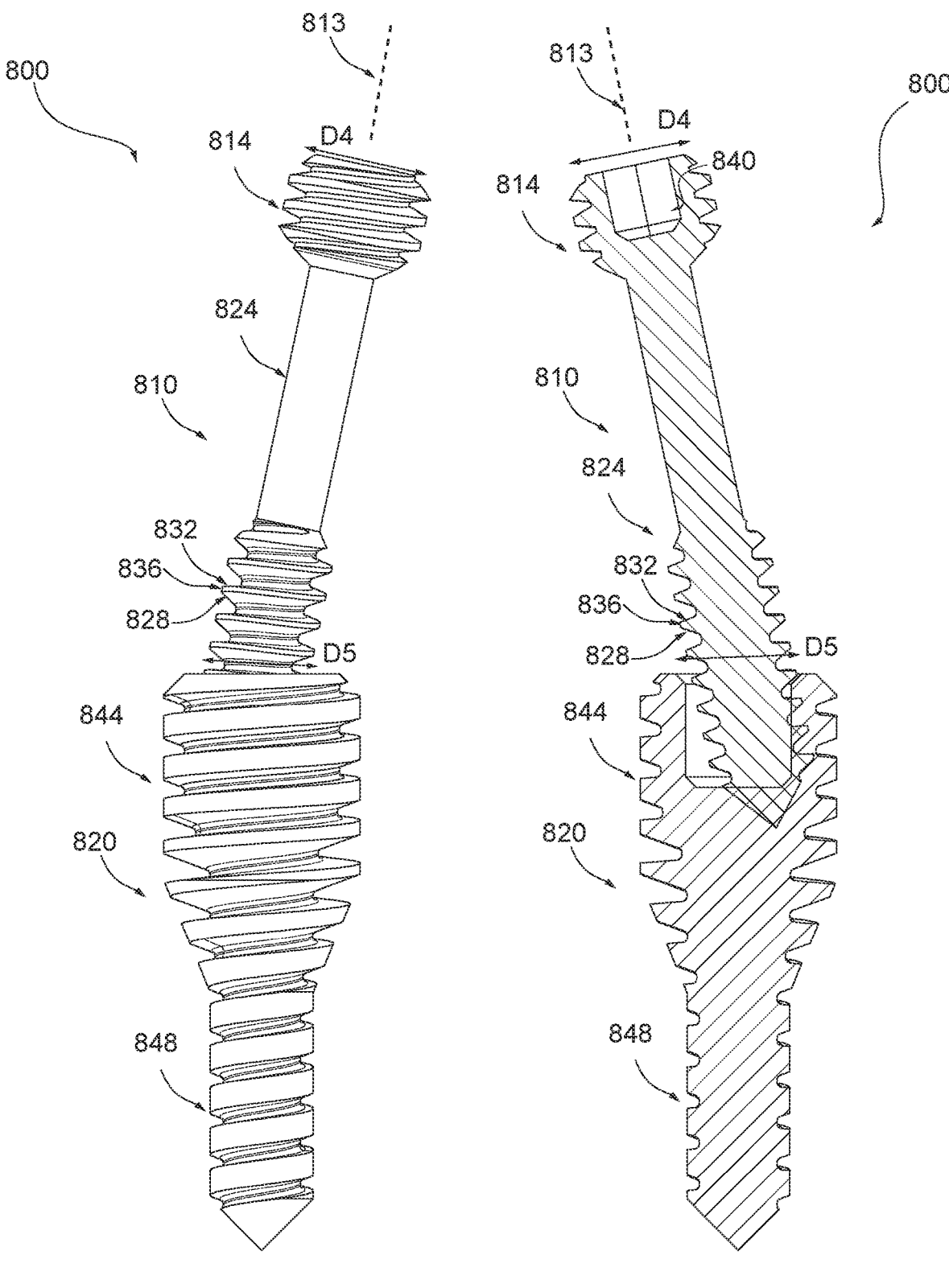
Fig. 72                 Fig. 73

BONE FIXATION SYSTEM AND DEVICE

TECHNICAL FIELD

The present disclosure relates generally to a bone fixation system, a bone fixation device, and related methods.

BACKGROUND

A common procedure for handling healing of broken bones and addressing deformities such as hammertoe is the use of bone fixation implants for fusing one or more adjacent bones. Conventional bone fixation implants utilize generic screws and wires that create a rigidly fused joint with very limited adjustability intraoperatively. Some implants offer some limited degree of flexibility and/or adjustment when used under very specific circumstances that require highly technical surgical procedures. Such existing bone fixation implants often require multiple components with many intricate mating features requiring customization depending on the type of bone, patient, or desired location of the implant in the body of a patient. This results in increased costs, less desirable healing outcomes, and multiple procedures to achieve a desired outcome.

Thus, there is still a need for a bone fixation implant capable of being implanted that addresses the aforementioned problems of conventional bone fixation implants including providing flexibility in bone-to-bone alignment with less invasive procedures that are pragmatic for the operating room and applicable for use with some of the smallest bones of the human anatomy.

SUMMARY

An embodiment of the present disclosure includes a bone fixation device. The bone fixation device includes a first bone anchor elongated along a first longitudinal axis for securing to a distal bone, a second bone anchor elongated along a second longitudinal axis for securing to a proximal bone, and a connector element removably secured to the first and second bone anchors.

Another embodiment of the disclosure is a method for fixing together one or more bone segments. The method includes attaching a first bone anchor to an end of a first bone of a patient, attaching a second bone anchor to an end of a second bone adjacent the first bone, inserting a connector element based on a desired orientation of the first bone relative to the second bone, and securing the connector element to the first bone anchor and the second bone anchor to secure the first bone and second bone in a fixed position.

Another embodiment includes a method for bone fixation. The method includes implanting a first bone anchor into a first bore of a first bone and a second bone anchor into a second bore of a second bone adjacent the first bone. The method further includes the steps of securing a connector element to the first bone anchor and the second bone anchor and applying a compression force to the first bone and second bone to lock the connector element in a fixed position relative to the first bone anchor and the second bone anchor.

Another embodiment of the present disclosure includes a bone fixation device. The bone fixation device includes a first bone anchor elongated along a first longitudinal axis for securing to a distal bone and a second bone anchor elongated along a second longitudinal axis for securing to a proximal bone. The first bone anchor includes a ball screw, and the second bone anchor includes a socket portion operatively connected to the ball screw. The ball screw is configured to be rotatably seated within the socket portion.

Another embodiment of the disclosure is a bone fixation device having a first bone anchor elongated along a first longitudinal axis for securing to a distal bone and a second bone anchor elongated along a second longitudinal axis for securing to a proximal bone. The first bone anchor includes a ball screw, and the second bone anchor includes a socket portion. The first bone anchor is threadedly secured to the second bone anchor.

Another embodiment of the disclosure is a bone fixation device having a first bone anchor elongated along a first longitudinal axis for securing to a distal bone and a second bone anchor elongated along a second longitudinal axis for securing to a proximal bone. The first bone anchor includes a first plurality of exterior threads, and the second bone anchor includes a second plurality of exterior threads. The first plurality of exterior threads is threadedly engaged to the second plurality of exterior threads for adjustably securing a position of the distal bone relative to the proximal bone.

Another embodiment of the disclosure is a bone fixation device. The bone fixation device includes a first bone anchor elongated along a first longitudinal axis for securing to a distal bone and a second bone anchor elongated along a second longitudinal axis for securing to a proximal bone. The first bone anchor is pivotably connected to the second bone anchor for adjustably securing a position of the distal bone relative to the proximal bone.

Another embodiment of the disclosure is a surgical instrument for fixing one or more bone segments together. The surgical instrument includes a curved elongated body having a first end and a second end opposite the first end. The surgical instrument further includes a first bone anchor adjustably mounted to the first end of the elongated body and a second bone anchor adjustably mounted to the second end of the elongated body. The first bone anchor is positioned at a desired joint location and the second bone anchor is positioned adjacent a tip of a distal bone spaced from the desired joint location.

Another embodiment of the present disclosure is a surgical instrument configured to prepare one or more bone segments of a joint for fusion. The surgical instrument includes an elongated shaft, an end portion about a first end of the elongated shaft for securing to a rotating instrument, a surgical cutting tool about a second end of the elongated shaft opposite the first end, and a flange member positioned along the elongated shaft between the end portion and the surgical cutting tool.

BRIEF DESCRIPTION OF THE DRAWINGS

The foregoing summary, as well as the following detailed description of exemplary embodiments of the present application, are better understood when read in conjunction with the appended drawings. For the purposes of illustrating the present application, there is shown in the drawings, exemplary embodiments of the disclosure. It should be understood, however, that the application is not limited to the precise arrangements and instrumentalities shown. In the drawings:

FIG. 33 is a perspective view of a first bone anchor of the bone fixation device shown in FIGS. 31-32;

FIG. 34 is a cross-sectional side view of the first bone anchor shown in FIG. 33;

FIG. 35 is a perspective view of a second bone anchor of the bone fixation device shown in FIGS. 31-32;

FIG. 36 is a cross-sectional perspective view of the second bone anchor shown in FIG. 35;

FIG. 37 is a perspective view of a compression member of the bone fixation device shown in FIGS. 31-32;

FIG. 49 is a perspective view of a second bone anchor of the bone fixation device shown in FIGS. 45-46B;

FIG. 50A is a side view of the second bone anchor shown in FIG. 49;

FIG. 50B is a cross-sectional side view of the second bone anchor shown in FIGS. 49-50A;

5

Figures 51, 52, 53:
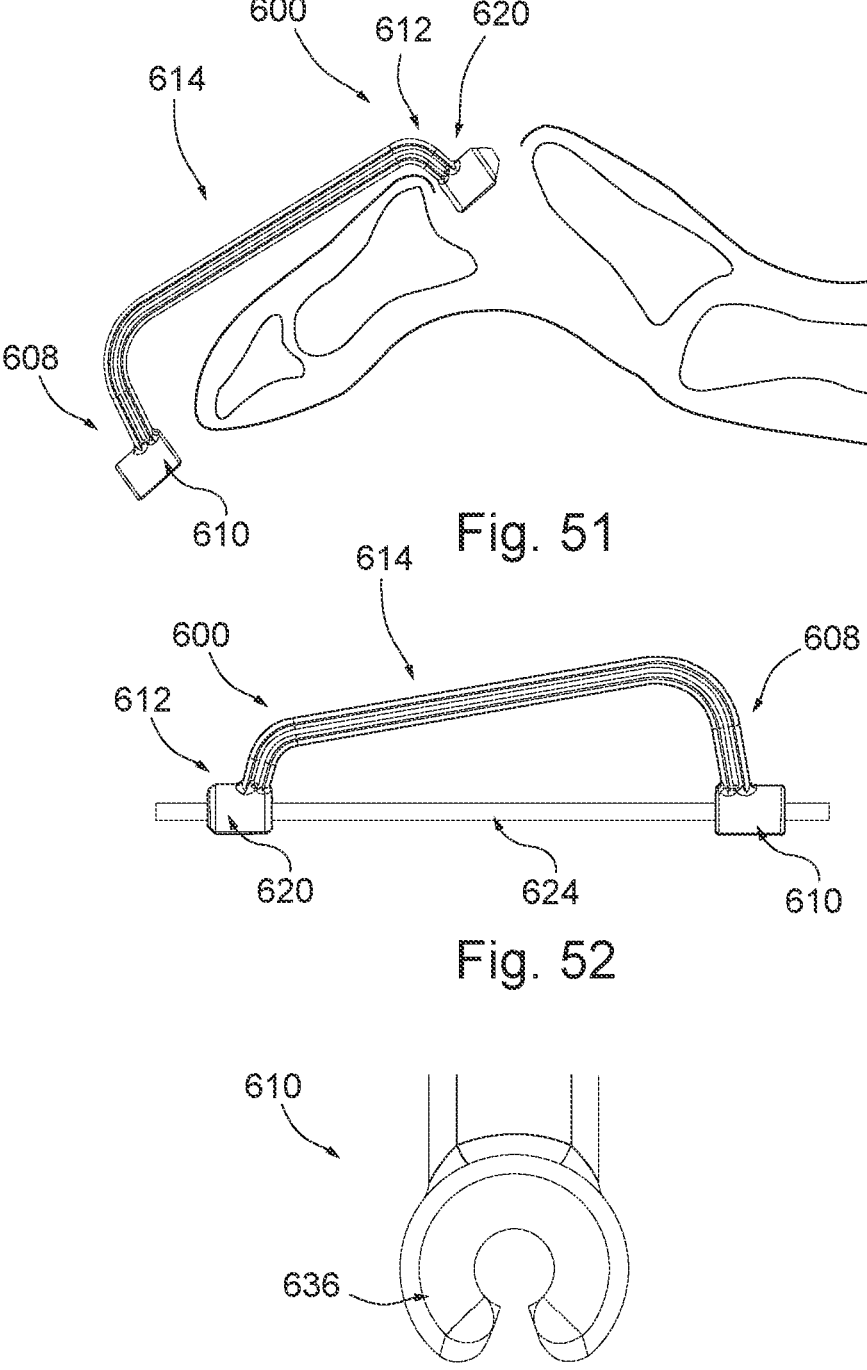
FIG. 51 is a schematic view of a surgical instrument inserted into a bone in accordance with an exemplary embodiment of the present disclosure.
FIG. 52 is a side view of the surgical instrument shown in FIG. 51.
Figures 54, 55, 56:
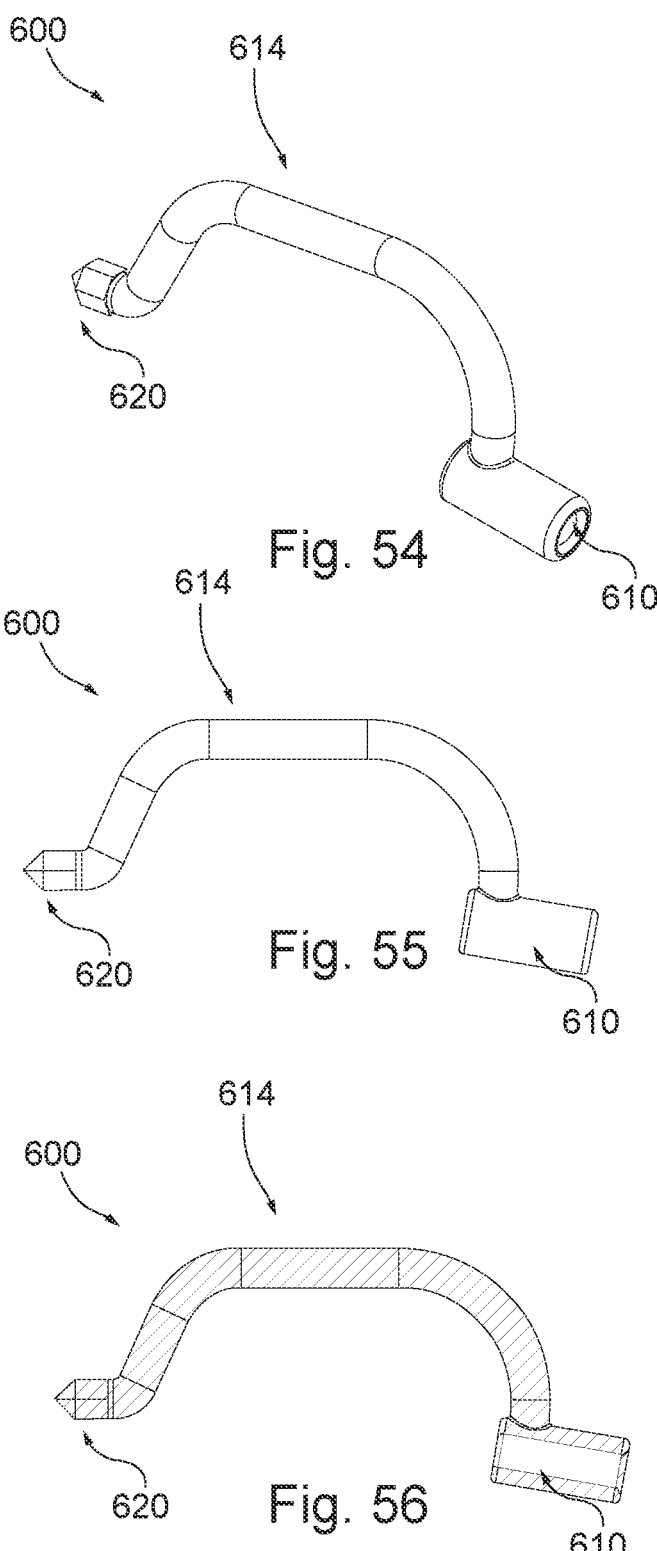
Figures 57, 58, 59:
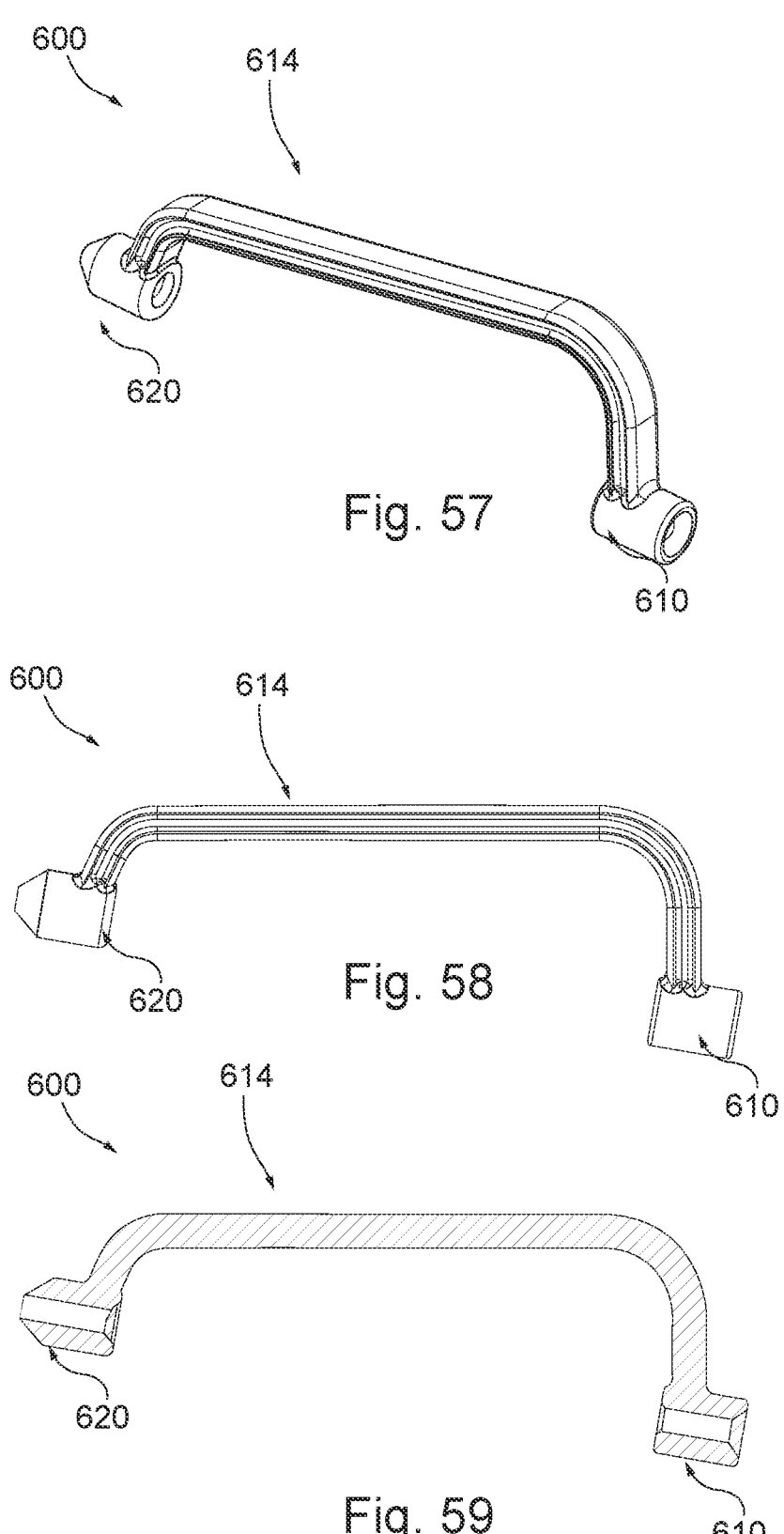
Figures 60, 61, 62, 63:
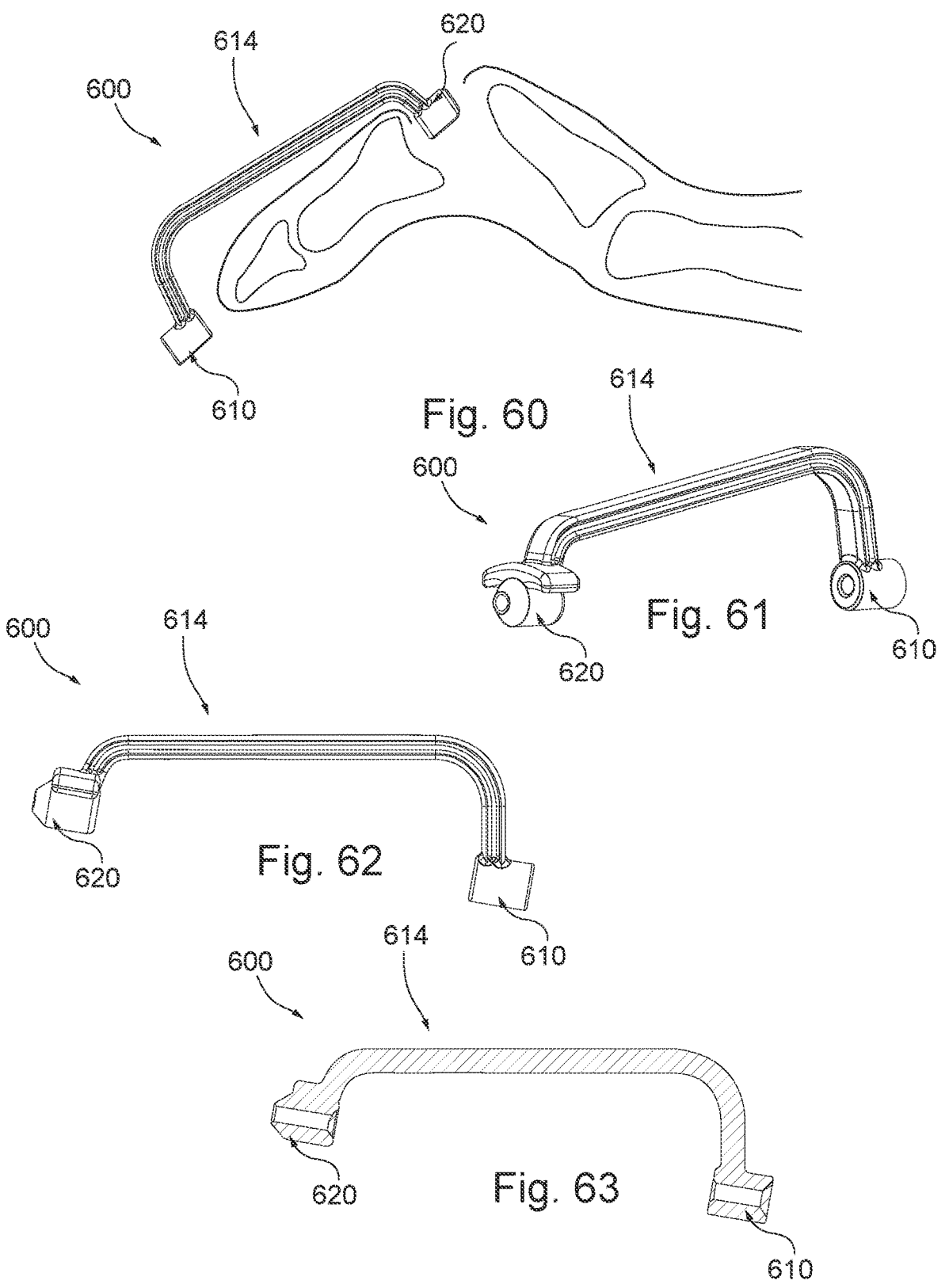
Figures 64, 65, 66:
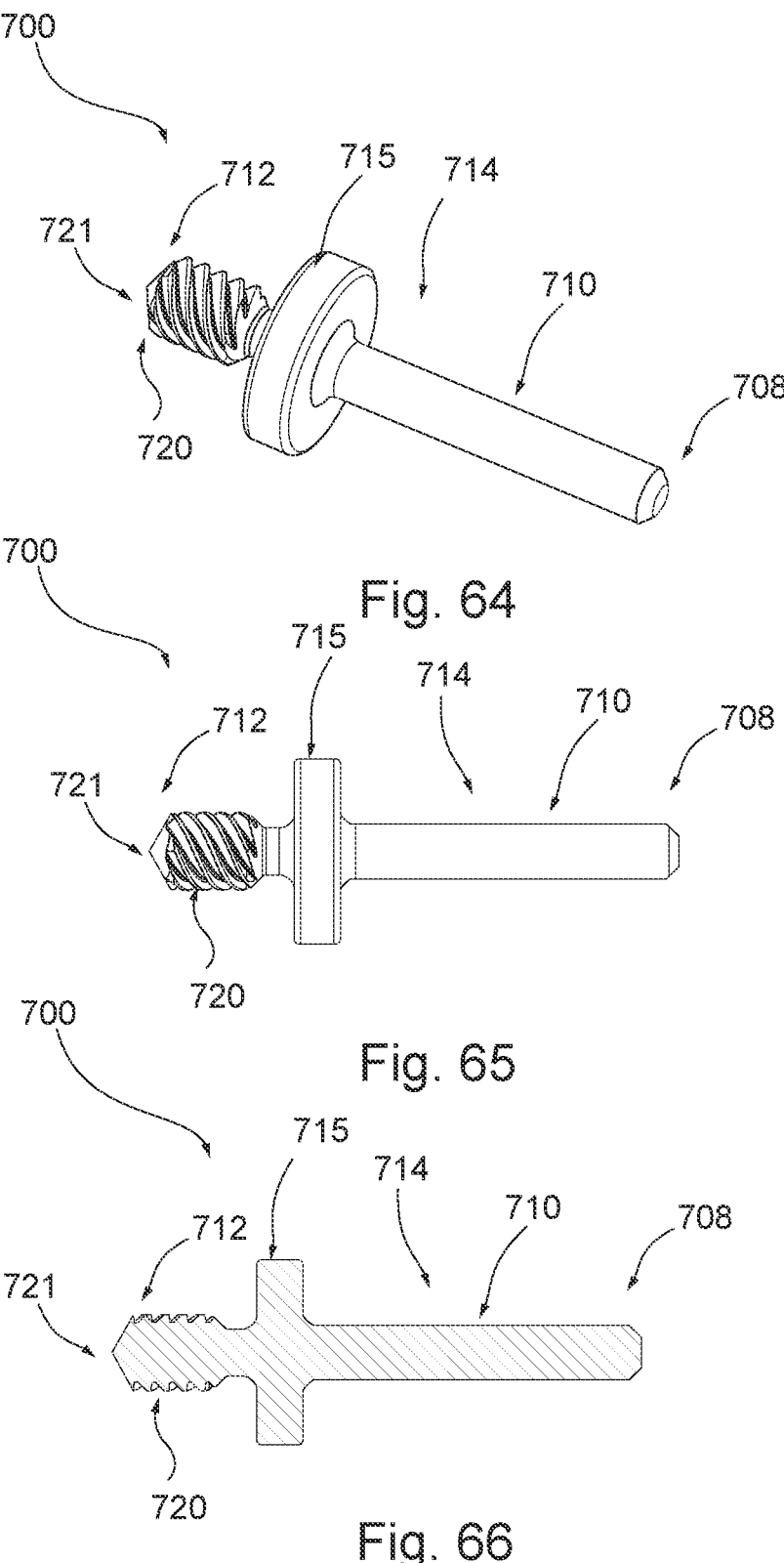
Figures 67, 68:
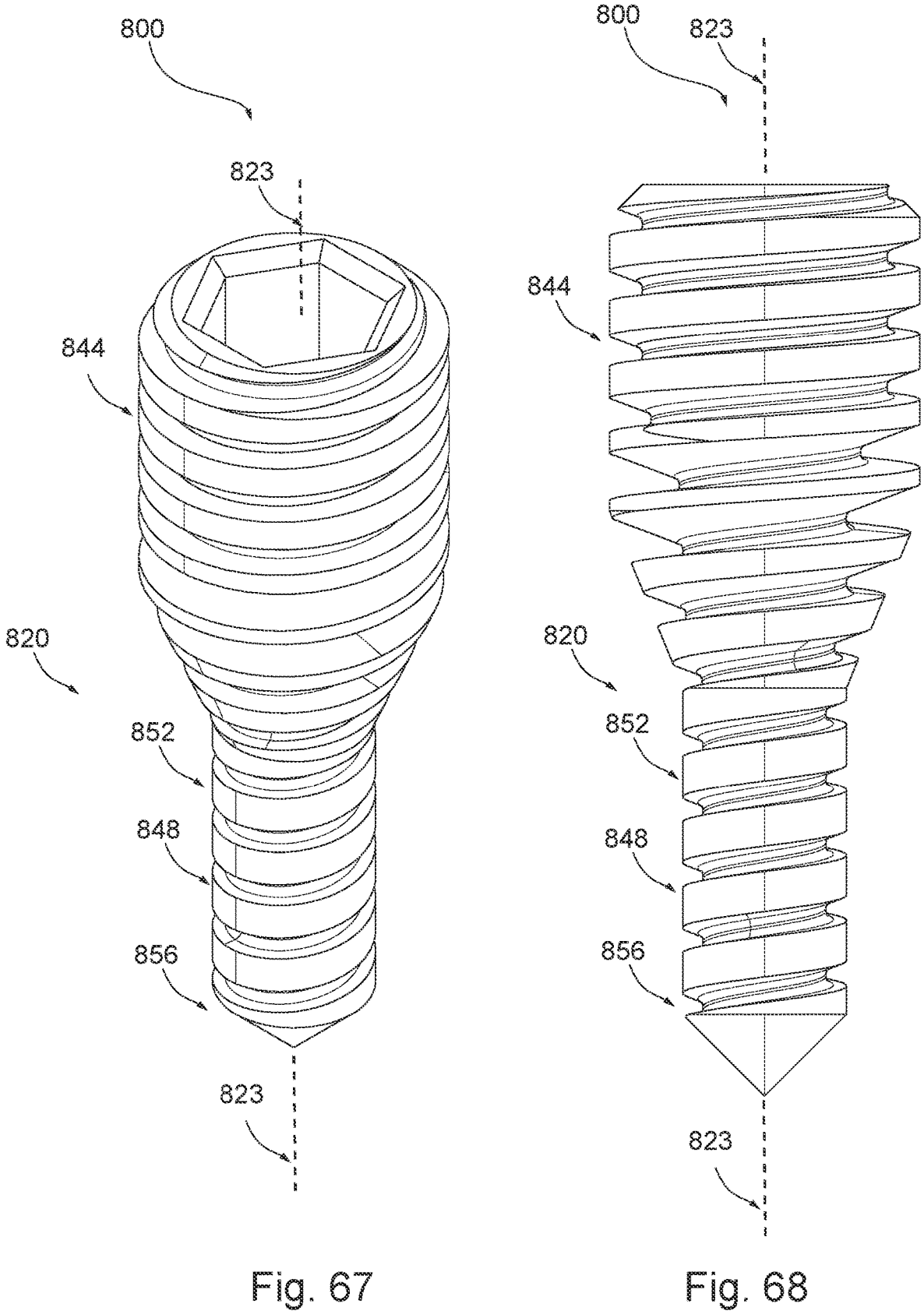
Figures 69, 70, 71:
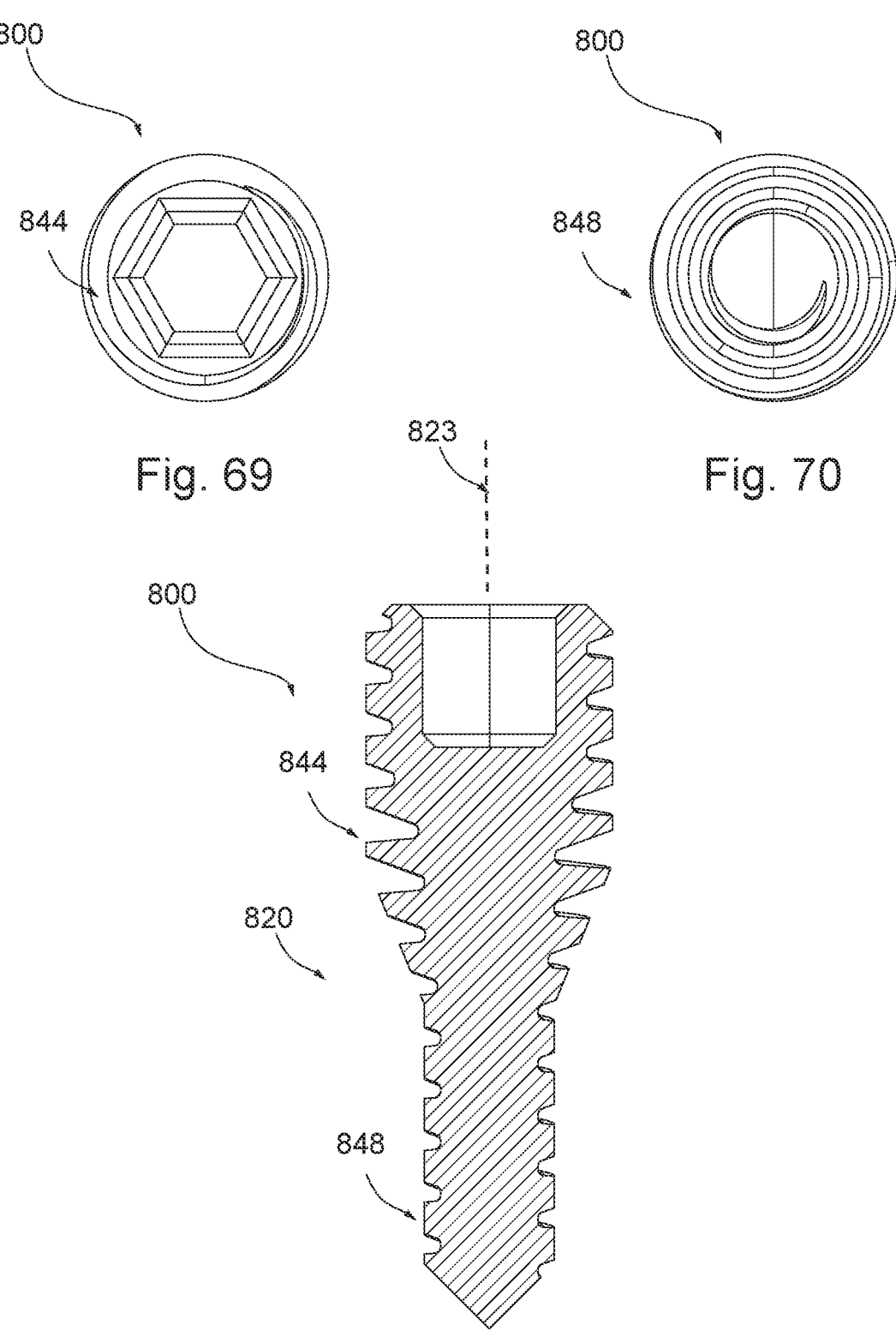
Figures 74, 75:
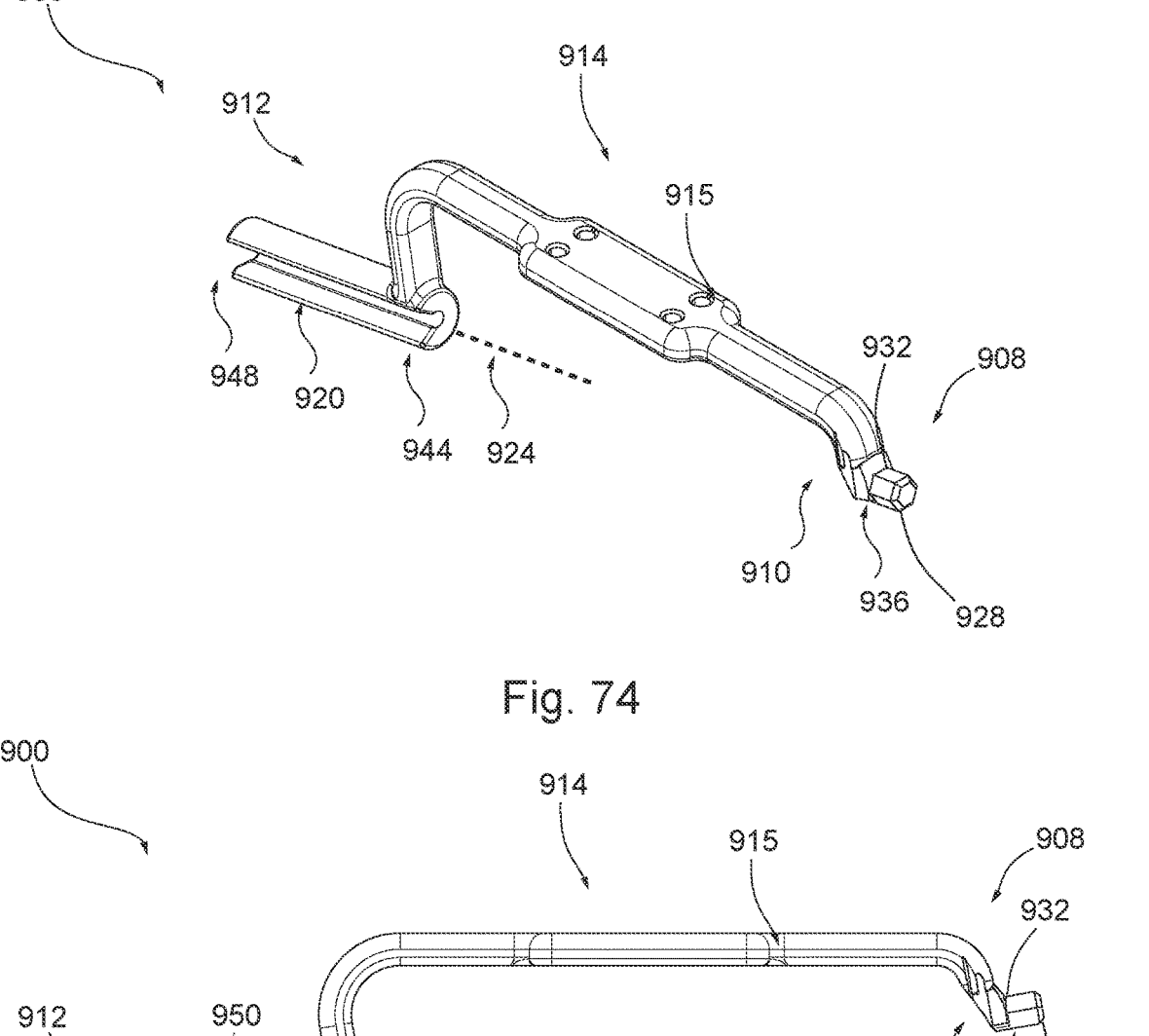
Figure 76:
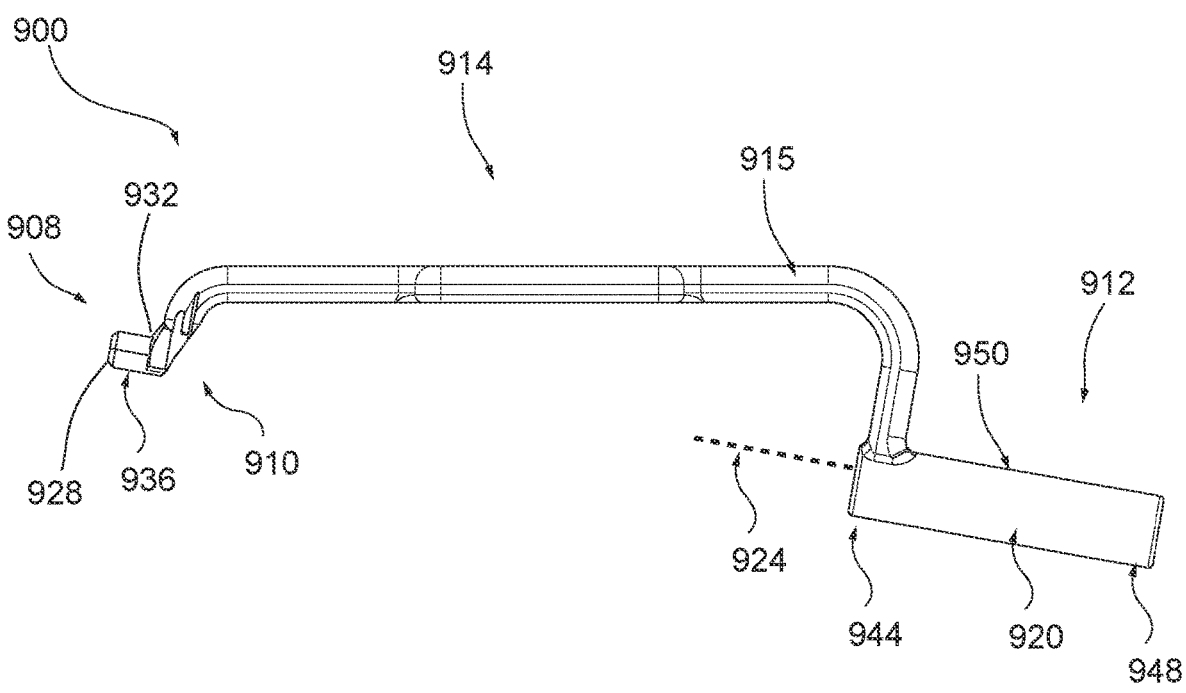
Figure 77:
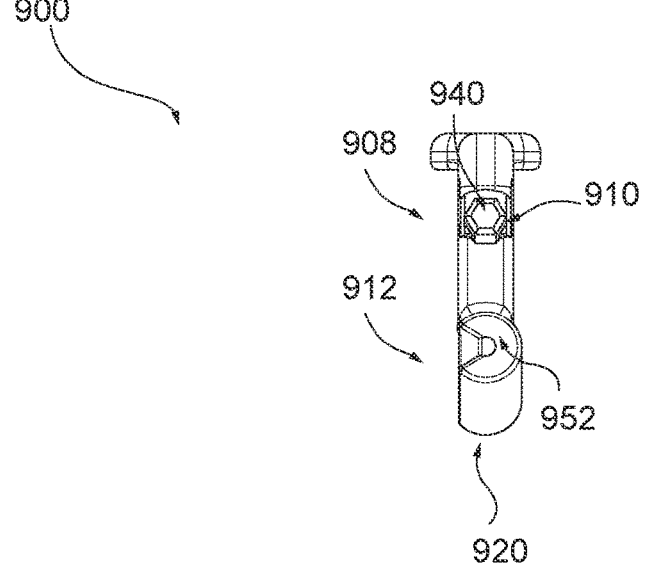
Figure 78:
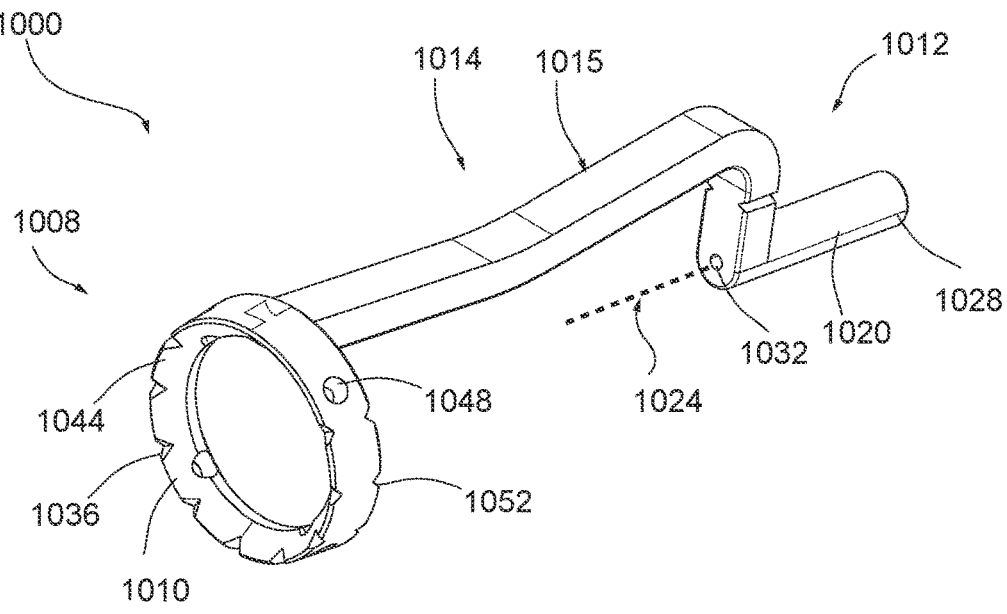
Figure 79:
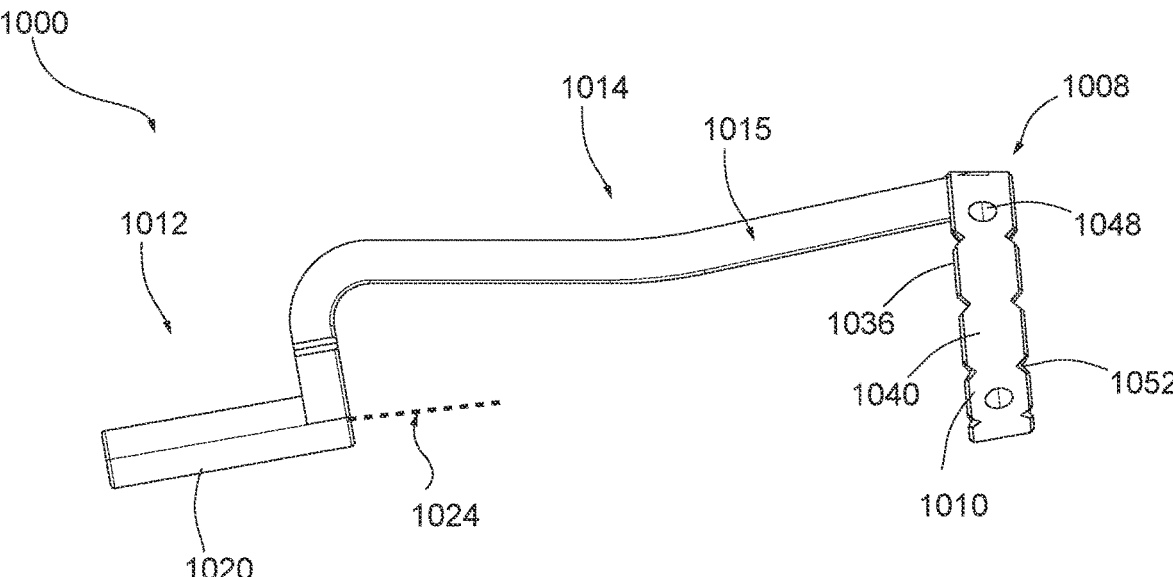
Figure 80:
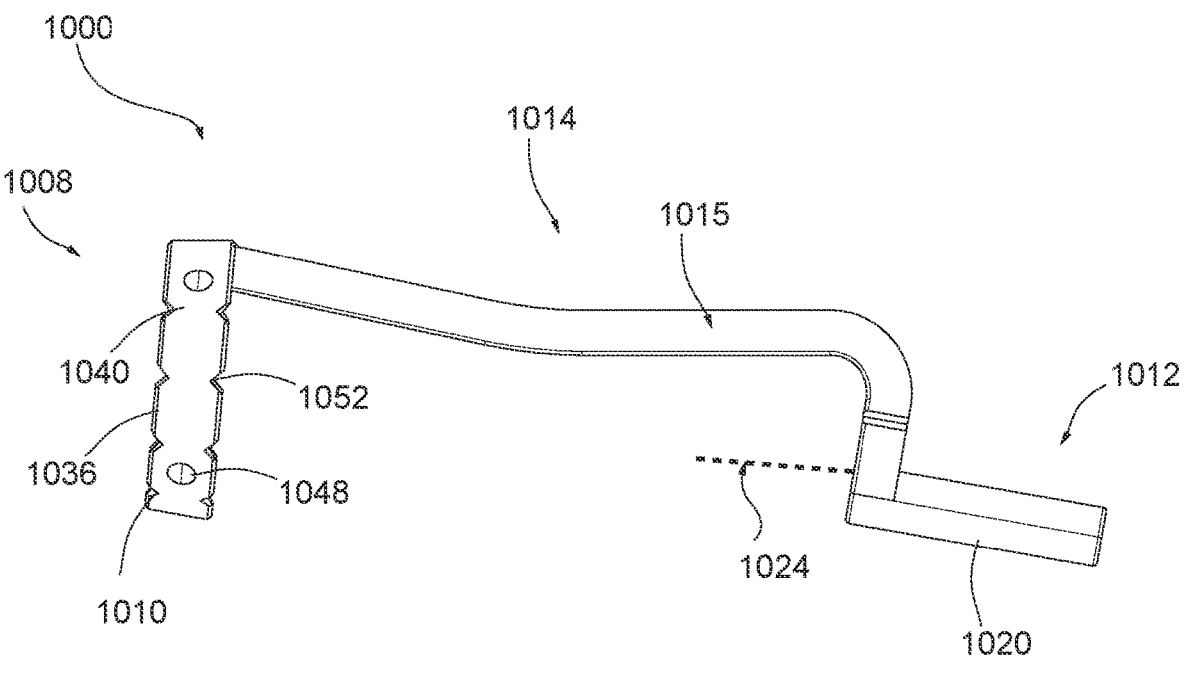
Figure 81:
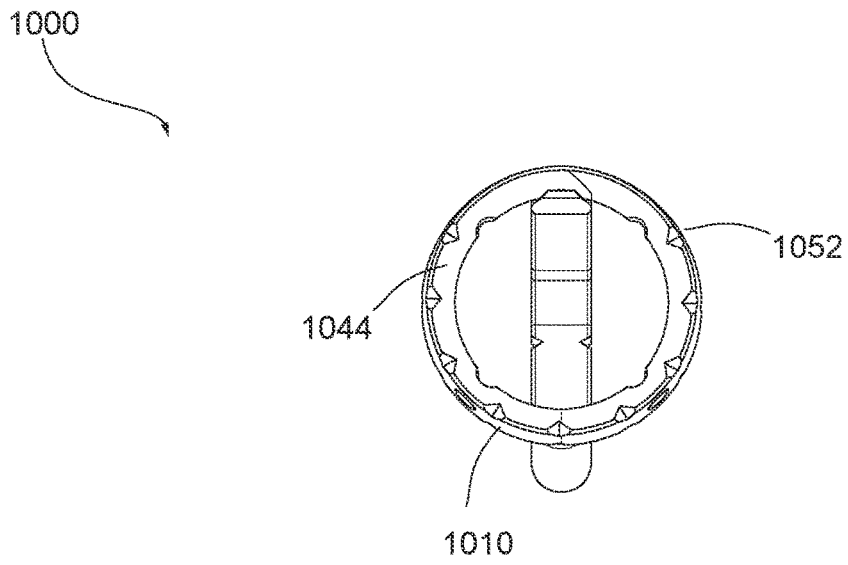

FIG. 53 is a front view of the surgical instrument shown in FIGS. 51-52;

FIG. 54 is a perspective view of a surgical instrument in accordance with an exemplary embodiment of the present disclosure;

FIG. 55 is a side view of the surgical instrument shown in FIG. 54;

FIG. 56 is a cross-sectional side view of the surgical instrument shown in FIGS. 54-55;

FIG. 57 is a perspective view of a surgical instrument in accordance with an exemplary embodiment of the present disclosure;

FIG. 58 is a side view of the surgical instrument shown in FIG. 57;

FIG. 59 is a cross-sectional side view of the surgical instrument shown in FIGS. 57-58;

FIG. 60 is a schematic view of a surgical instrument inserted into a bone in accordance with an exemplary embodiment of the present disclosure;

FIG. 61 is a perspective view of the surgical instrument shown in FIG. 60;

FIG. 62 is a side view of the surgical instrument shown in FIGS. 60-61;

FIG. 63 is a cross-sectional side view of the surgical instrument shown in FIGS. 60-62;

FIG. 64 is a schematic view of a surgical instrument in accordance with an exemplary embodiment of the present disclosure;

FIG. 65 is a side view of the surgical instrument shown in FIG. 64;

FIG. 66 is a cross-sectional side view of the surgical instrument shown in FIGS. 64-65;

FIG. 67 is a perspective view of a bone fixation device in accordance with an exemplary embodiment of the present disclosure;

FIG. 68 is a side view of the bone fixation device shown in FIG. 67;

FIG. 69 is a top view of the bone fixation device shown in FIGS. 67-68;

FIG. 70 is a bottom view of the bone fixation device shown in FIGS. 67-69;

FIG. 71 is a cross-sectional side view of the bone fixation device shown in FIGS. 67-71;

FIG. 72 is a side view of a bone fixation device in accordance with an exemplary embodiment of the present disclosure;

FIG. 73 is a cross-sectional side view of the bone fixation device shown in FIG. 72;

FIG. 74 is a perspective view of a surgical instrument in accordance with an exemplary embodiment of the present disclosure;

FIG. 75 is a side view of the surgical instrument shown in FIG. 74;

FIG. 76 is an opposing side view of the surgical instrument shown in FIGS. 74-75;

FIG. 77 is a front view of the surgical instrument shown in FIGS. 74-76;

FIG. 78 is a perspective view of a surgical instrument in accordance with an exemplary embodiment of the present disclosure;

FIG. 79 is a side view of the surgical instrument shown in FIG. 78;

FIG. 80 is an opposing side view of the surgical instrument shown in FIGS. 78-79;

FIG. 81 is a front view of the surgical instrument shown in FIGS. 78-80;

6

Figures 82, 83:
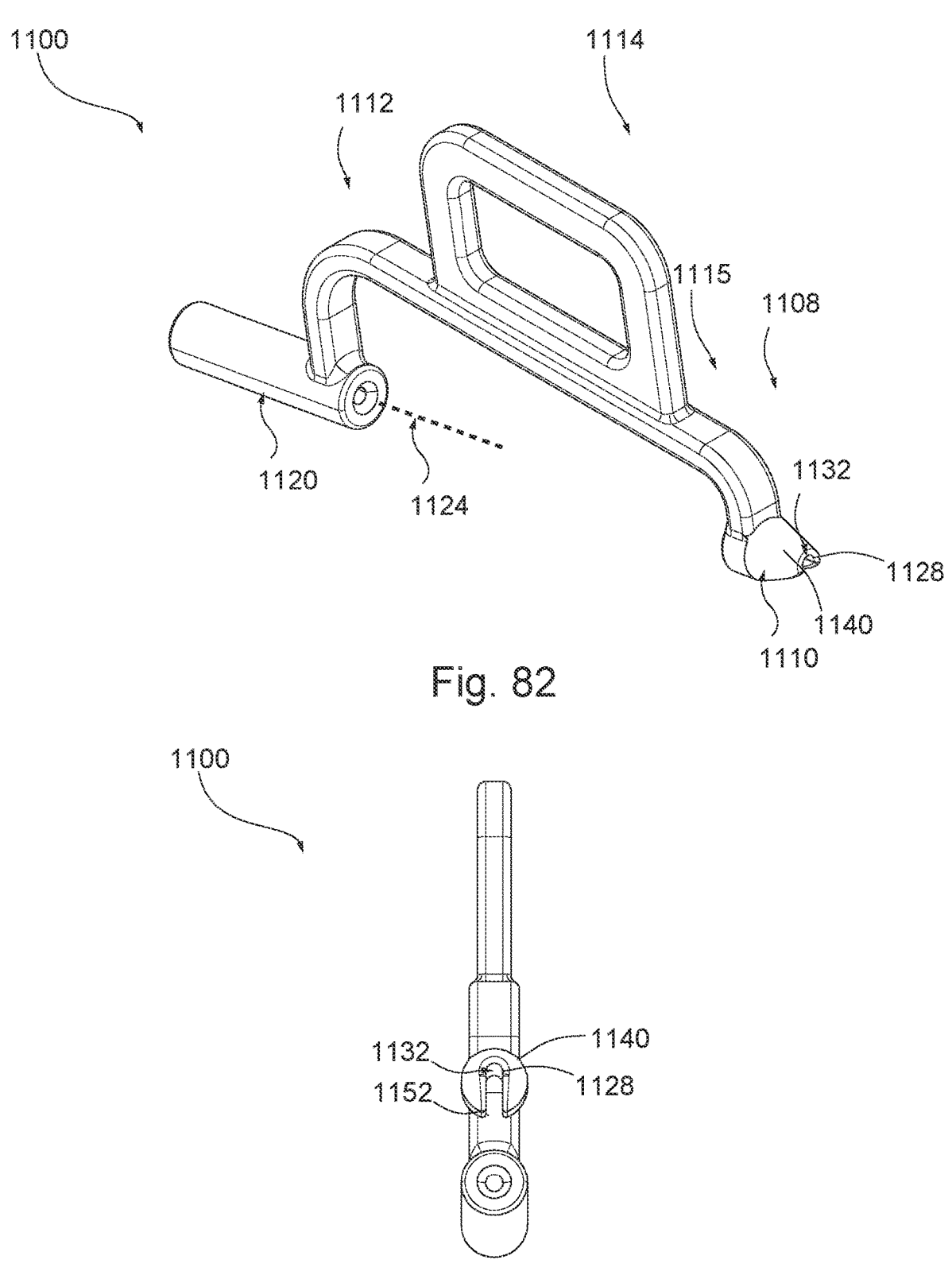
Figures 84, 85:
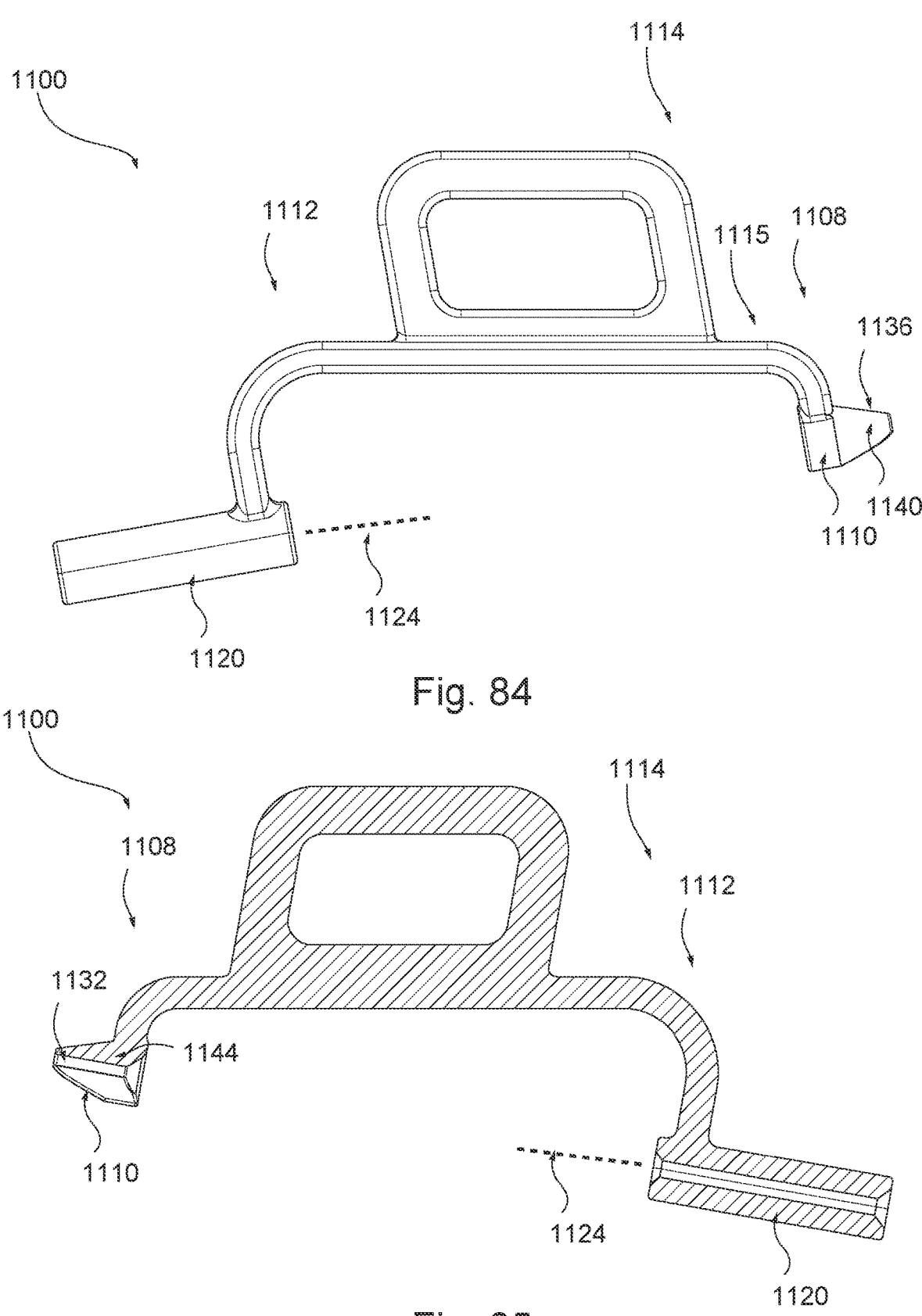

FIG. 82 is a perspective view of a surgical instrument in accordance with an exemplary embodiment of the present disclosure;

FIG. 83 is a front view of the surgical instrument shown in FIG. 82;

FIG. 84 is a side view of the surgical instrument shown in FIGS. 82-83; and FIG. 85 is an opposing cross-sectional side view of the surgical instrument shown in FIGS. 82-84.

DETAILED DESCRIPTION OF ILLUSTRATIVE EMBODIMENTS

Bone fixation devices as described are configured for aid in the fixation of two or more bones or bone segments. In one example, the bone fixation system and device as described herein are configured fixation of hammertoe. In other example, the bone fixation system and devices are configured for interphalangeal joint fixation. For example, the bone fixation devices may be used for fixation of metatarsals, proximal phalanges, middle phalanges, or distal phalanges. While the embodiments described are configured for interphalangeal joint fixation, it is possible that the described embodiments could be configured for fixation of phalanges, metatarsals, cuneiform, or cuboid bones in the foot. In other embodiments, the bone fixation devices may be configured for fixation of bone segments of phalanges, metatarsals or other bones in the hand.

Referring to FIGS. 1-15, there is shown an exemplary embodiment of a bone fixation system that includes a bone fixation device and one or more instruments for use in bone fixation. As shown, bone fixation device 100 includes a first bone anchor 110, a second bone anchor 120, and a connector element 130 removably secured to the first and second bone anchors. The first bone anchor 110 is elongated along a first longitudinal axis 113 and is configured to attach to a distal bone. Similarly, the second bone anchor 120 is elongated along a second longitudinal axis 123 and is configured to attach to a proximal bone.

The bone fixation device 100 can be manufactured from a number of materials including nitinol, titanium alloys, non-titanium alloys, or other polymeric materials, e.g., plastics, plastic composites, polyetheretherketone (PEEK), and ceramics such as silicon nitride, zirconium oxide, silver oxide, and other suitable materials, both radiopaque and radiolucent.

The first bone anchor 110 is connected to a distal bone (not shown) and the second bone anchor 120 is connected to a proximal bone (not shown). As described below, the first bone anchor 110 and the second bone anchor 120 may include similar features and a discussion of such features are applicable to both the first and second bone anchors, unless stated otherwise.

Referring now to FIGS. 1-11, the first bone anchor 110 is generally an elongated body having the longitudinal axis 113. The first bone anchor 110 is preferably a cylindrical member having a circular cross section, however the first bone anchor 110 can have any shape cross section such as hexagonal, polygonal or any other shape suitable for its intended purpose. The first bone anchor 110 can be formed with a plurality of segmented portions having different cross-sectional diameters. However, the first bone anchor 110 preferably has a uniform cross-sectional diameter.

The first bone anchor 110 includes a first outer thread portion 112 for threadedly securing the first bone anchor to the distal bone. Specifically, the first outer thread portion 112 is sized and shaped to be threadedly engaged within a bone canal or bore drilled into the distal bone prior to implantation of the first bone anchor. It is contemplated that the first bone anchor 110 has a tapering frustoconical shaped tip 107 to facilitate its attachment to the distal bone. The first bone anchor 110 further includes a first channel 111 shaped to receive a connector element.

The second bone anchor 120 is sized and shaped similar to the first bone anchor 110. That is, the second bone anchor 120 is generally an elongated body having the longitudinal axis 123. The second bone anchor 120 is preferably a cylindrical member having a circular cross section, however the second bone anchor 120 can also have any shape cross section suitable for its intended purpose of securing to the proximal bone.

Similarly, the second bone anchor 120 includes a second outer thread portion 122 for threadedly securing the second bone anchor 120 to the proximal bone. Specifically, the second outer thread portion 122 is sized and shaped to be threadedly engaged within a bone canal or bore drilled into the proximal bone prior to implantation of the second bone anchor 120. It is contemplated that the second bone anchor 120 has a tapering frustoconical shaped tip 106 to facilitate its attachment to the proximal bone. The second bone anchor 120 further includes a second channel 121 shaped to receive a connector element.

Figure 1A:
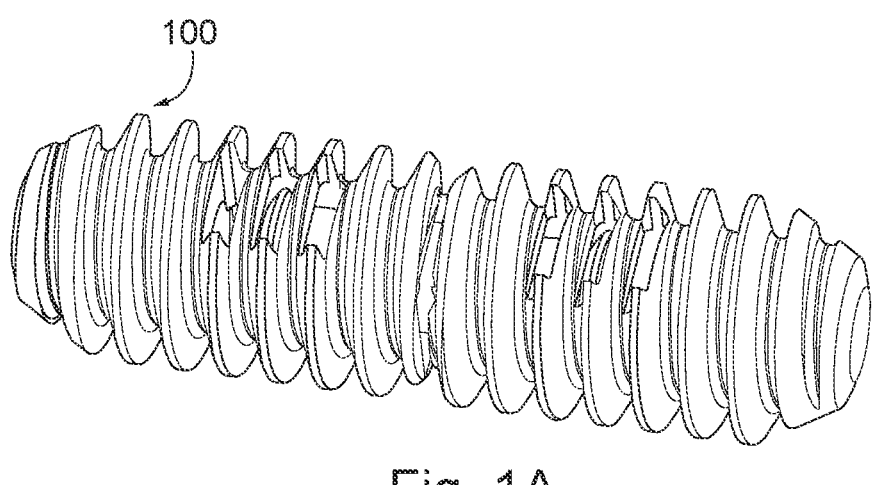
FIG. 1A is a perspective view of a bone fixation device in accordance with an exemplary embodiment of the present disclosure.
Figure 1B:
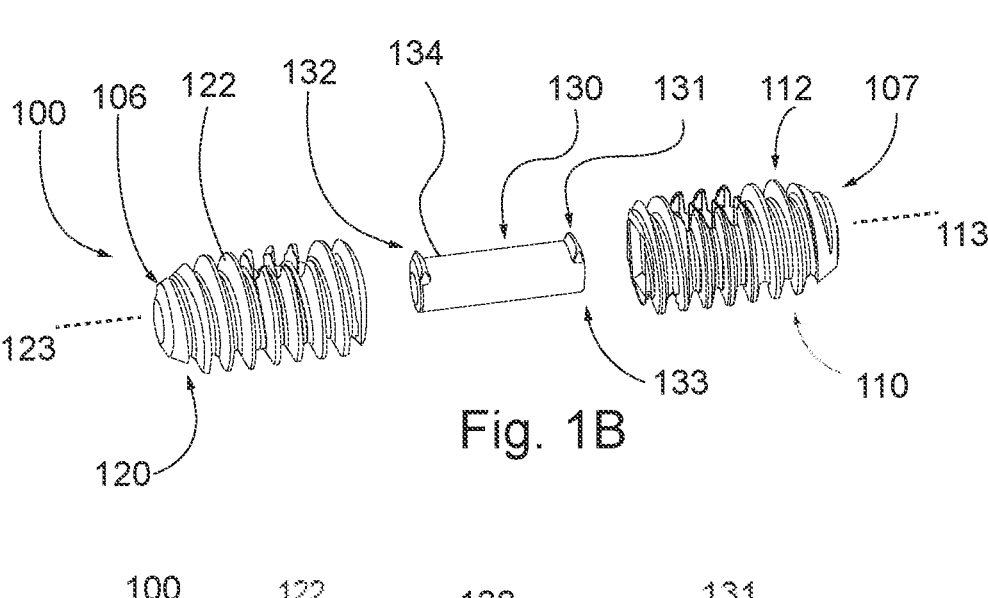
FIG. 1B is a an exploded perspective view of the bone fixation device shown in FIG. 1A.
Figure 2:
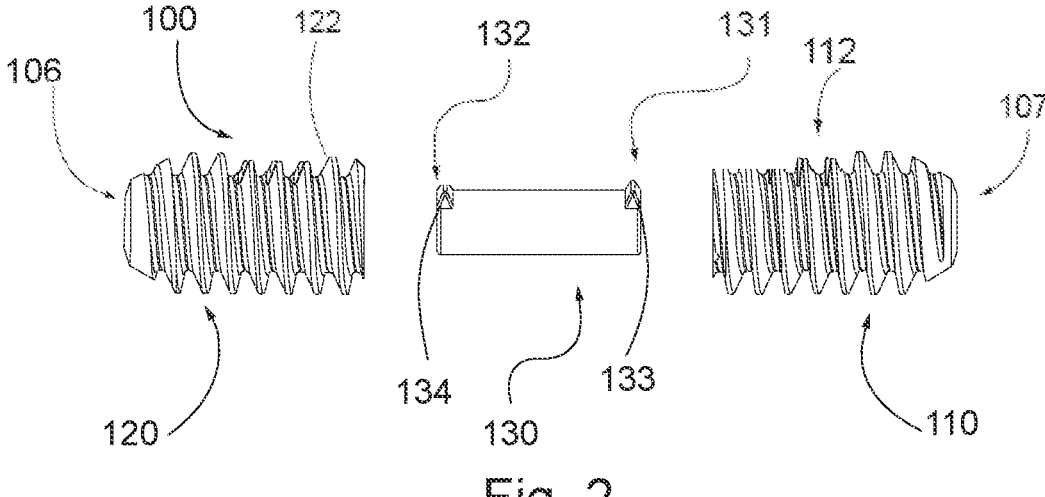
FIG. 2 is an exploded side view of the bone fixation device shown in FIGS. 1A-1B.
Figure 3:
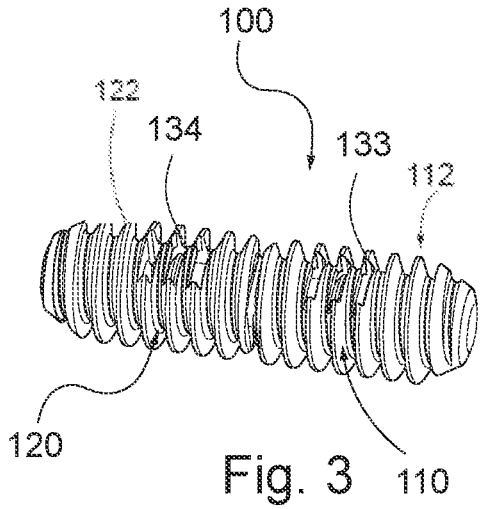
FIG. 3 is another perspective view of the bone fixation device shown in FIGS. 1A-2.
Figure 4:
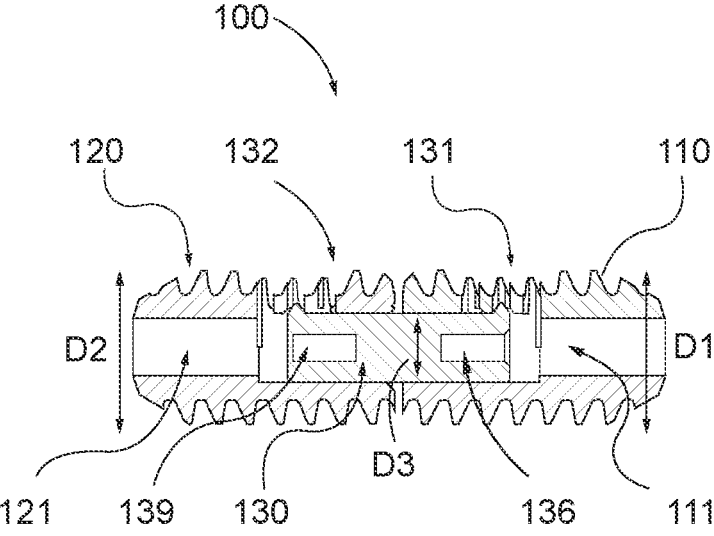
FIG. 4 is a cross-sectional side view of the bone fixation device shown in FIGS. 1A-3.
Figures 5A, 5B, 5C:
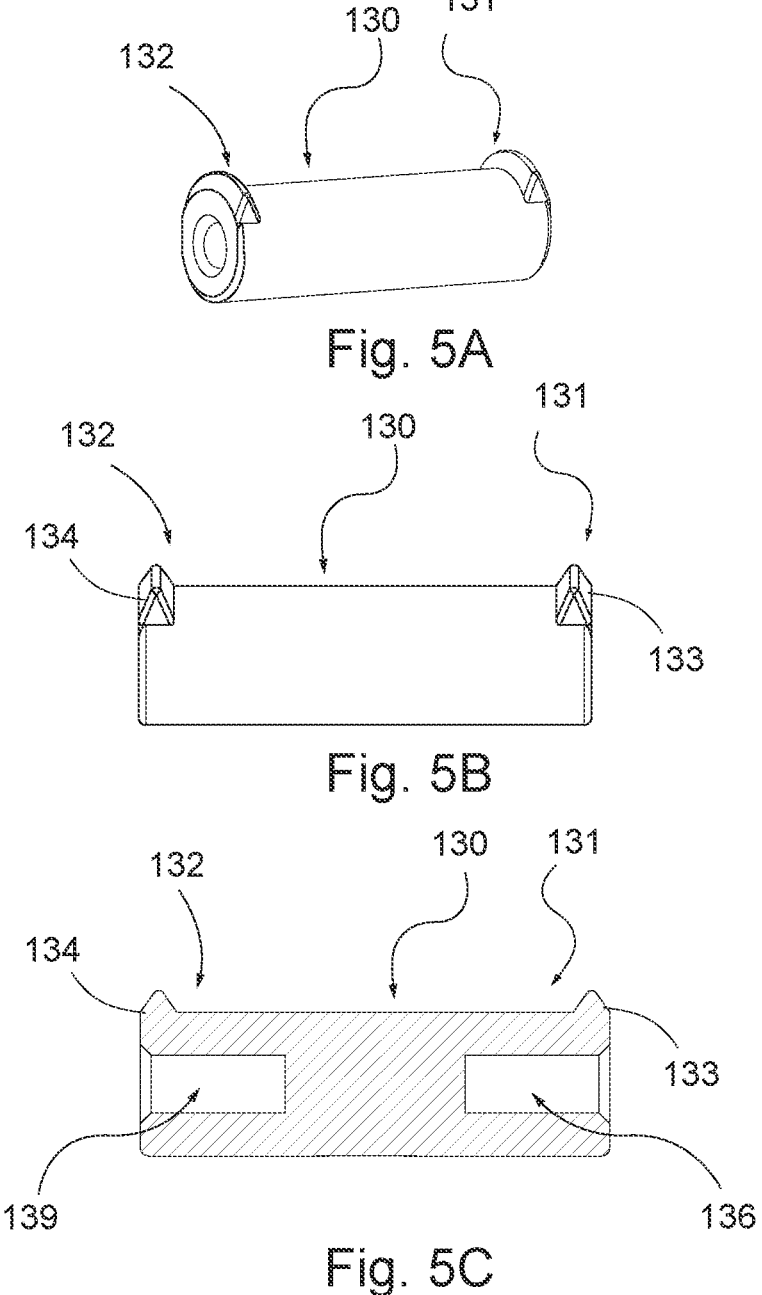
FIG. 5A is a perspective view of a connector element of the bone fixation device shown in FIGS. 1A-4.
FIG. 5B is a side view of the connector element shown in FIG. 5A.
FIG. 5C is a cross-sectional side view of the connector element shown in FIGS. 5A-5B.
Figure 6A:
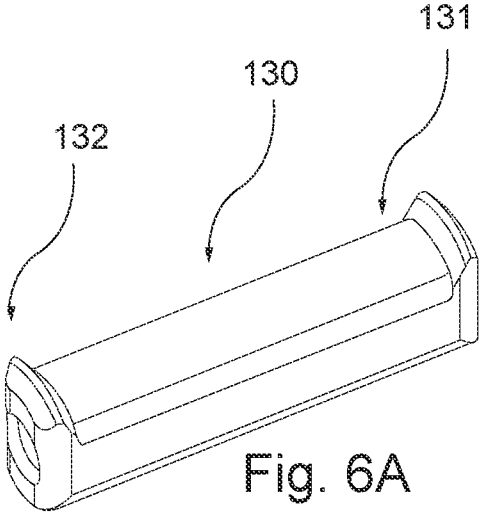
FIG. 6A is a perspective view of another connector element of the bone fixation device shown in FIGS. 1A-4.
Figure 6B:
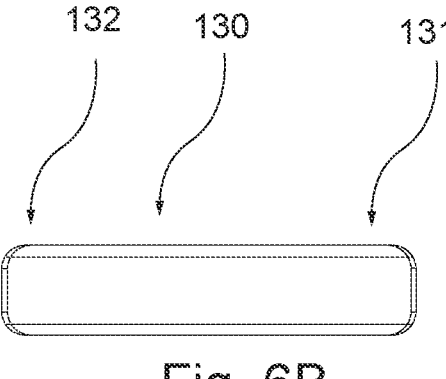
FIG. 6B is a bottom view of the connector element shown in FIG. 6A.
Figure 6C:
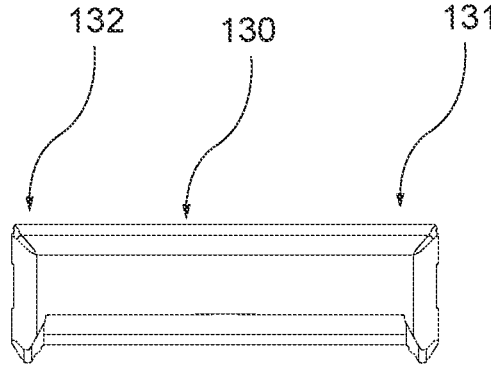
FIG. 6C is a top view of the connector element shown in FIGS. 6A-6B.
Figure 7:
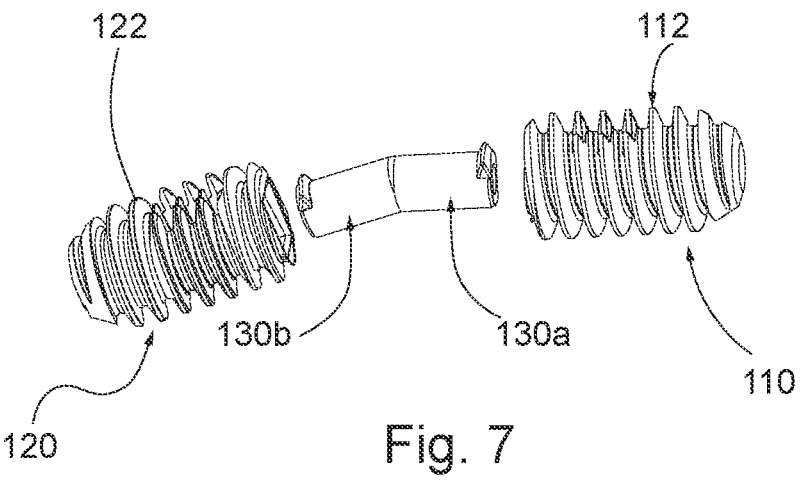
FIG. 7 is an exploded side view of the bone fixation device shown in FIGS. 1A-4 having a connector element in accordance with an exemplary embodiment of the present disclosure.

As discussed above, the connector element 130 is removably secured to the first and second bone anchors. As shown in FIGS. 1, 2, 4, 5, and 6, the connector element 130 is an elongated cylindrical member having a circular cross section. Specifically, a first end 131 of the connector element 130 is configured to be received within the first channel 111 of the first bone anchor 110. A second end 132 of the connector element 130 is configured to be received within the second channel 121 of the second bone anchor 120. It is to be understood that the first and second channels 111, 121 are complementary and correspondingly shaped to the respective first and second ends 131, 132 of the connector element 130. In other words, the connector element 130 correspondingly mates with respective ends of the first and second bone anchors 110, 120. As shown in FIGS. 4 and 6, the connector element 130 includes a pair of cannulated recesses 136, 139 located about respective ends of the connector element 130. In another embodiment, the connecter element 130 includes a single cannula.

Similar to the other components of the bone fixation device 100, the connector element 130 can be formed from nitinol or another shape memory alloy to induce compression across a desired fixation location in the body of a patient.

The connector element 130 correspondingly mates with the first and second bone anchors 110, 120 via a pair of ridges 133, 134 on the respective ends of the connector element that sit in the first channel 111 and the second channel 121, respectively. In accordance with another aspect, the first end 131 or second end 132 of the connector element 130 is configured to slideably engage the respective first and second bone anchors 110, 120. That is, the ridges 134,134 of the connector element 130 are configured to be press fit into the respective first channel 111 or second channel 121 of the bone anchors. In accordance with yet another aspect, the first channel 111 includes a first plurality of inner threads (not shown) configured to threadedly engage a corresponding plurality of threads (not shown) on the connector element 130. Similarly, the second channel 121 includes a second plurality of inner threads (not shown) configured to threadedly engage a corresponding plurality of threads (not shown) on the connector element 130.

In general, it is to be understood that the first and second bone anchors 110, 120 can correspondingly mate with the connector element 130 with a plurality of different mating features including, but not limited to, corresponding threads, barbs, protrusions, grooves, fasteners and the like. Similarly, the first and second bone anchors 110, 120 can also be correspondingly secured to the distal and proximal bones via a plurality of different mating features including, but not limited to, threads, barbs, protrusions, fasteners and the like. For example, the inner surface of the first bone anchor along the first channel includes a first inner mating feature configured to engage a first mating element of the connector element. Likewise, the inner surface of the second bone anchor along the second channel includes a second mating feature configured to engage a second mating element of the connector element. The mating feature and mating elements can be any of the mating features described above.

As shown in FIG. 4, the first bone anchor 110 has a first outer diameter $D_1$, the second bone anchor 120 has a second outer diameter $D_2$, and the connector element 130 has a third outer diameter $D_3$ less than the first and second outer diameters $D_1$, $D_2$ such that the connector element 130 is fully enclosed within the first and second channels 111, 121.

In accordance with an aspect best shown in FIGS. 1-6, the connector element 130 is of unitary construction wherein the first longitudinal axis 113 of the first bone anchor 110 is coaxial to the second longitudinal axis 123 of the second bone anchor 120 when the first and second bone anchors 110, 120 are matingly engaged with the connector element 130. However, as shown in FIGS. 7-11, the connector element 130 can be of modular construction. That is, the connector element 130 includes a first segment 130a coupled to the first bone anchor 110 and a second segment 130b coupled to the second bone anchor 120. The first and second segments 130a and 130b can be angularly offset with respect to each other, as shown.

Figure 9:
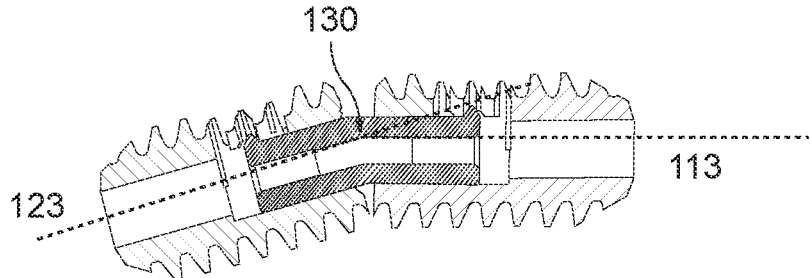
FIG. 9 is a cross-sectional side view of the bone fixation device shown in FIGS. 7-8.
Figure 10:
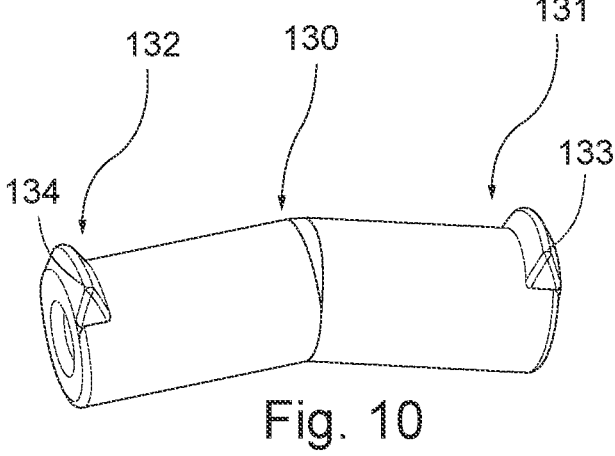
FIG. 10 is a perspective view of a connector element of the bone fixation device shown in FIGS. 7-9.
Figure 11:
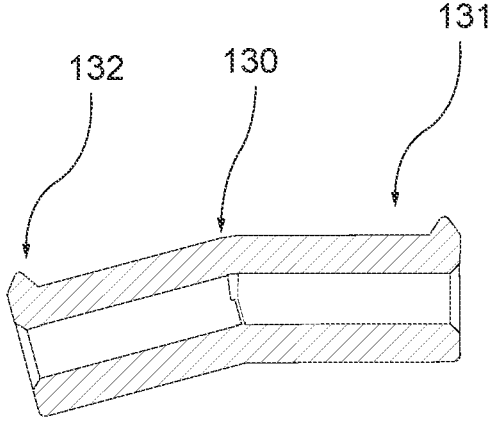
FIG. 11 is a cross-sectional perspective view of the connector element shown in FIG. 10.
Figure 12:
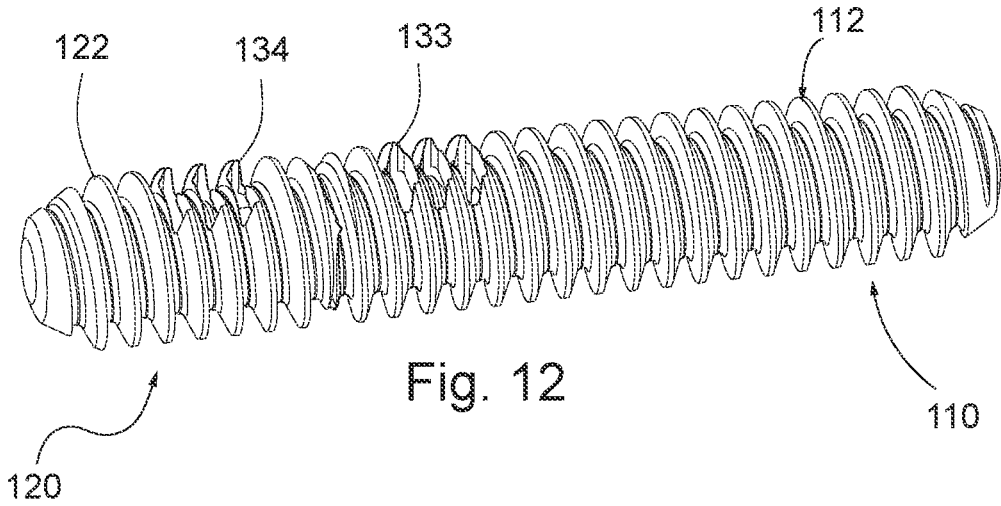
FIG. 12 is another perspective view of the bone fixation device shown in FIGS. 1A-4 in accordance with an exemplary embodiment of the present disclosure.
Figure 13:
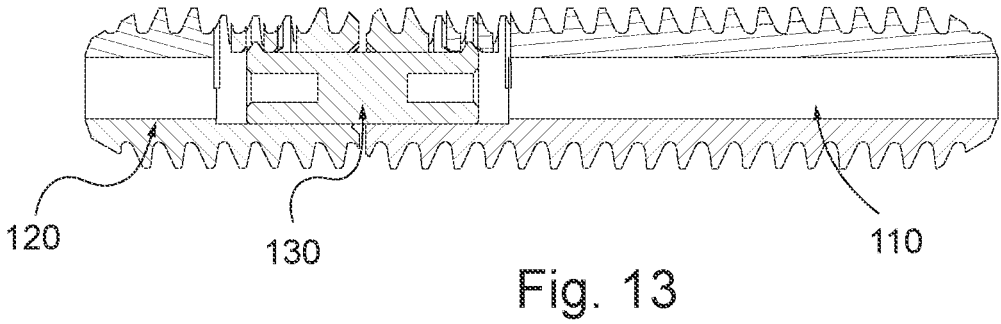
FIG. 13 is a cross-sectional side view of the bone fixation device shown in FIG. 12.
Figure 14:
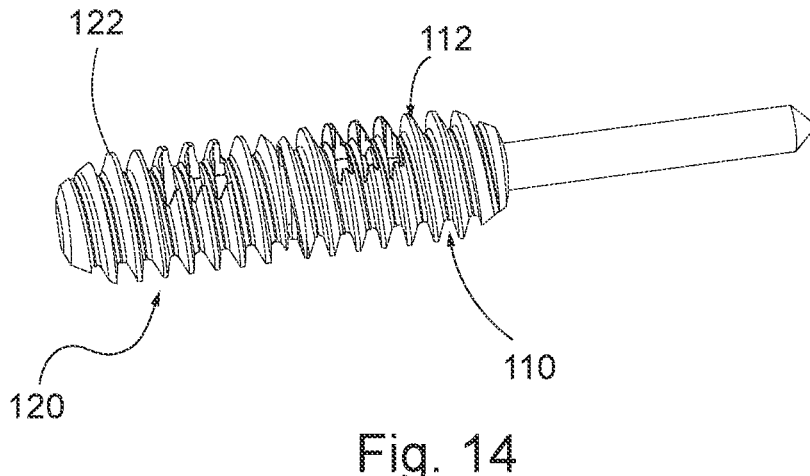
FIG. 14 is another perspective view of the bone fixation device shown in FIGS. 1A-4 in accordance with an exemplary embodiment of the present disclosure.
Figure 15:
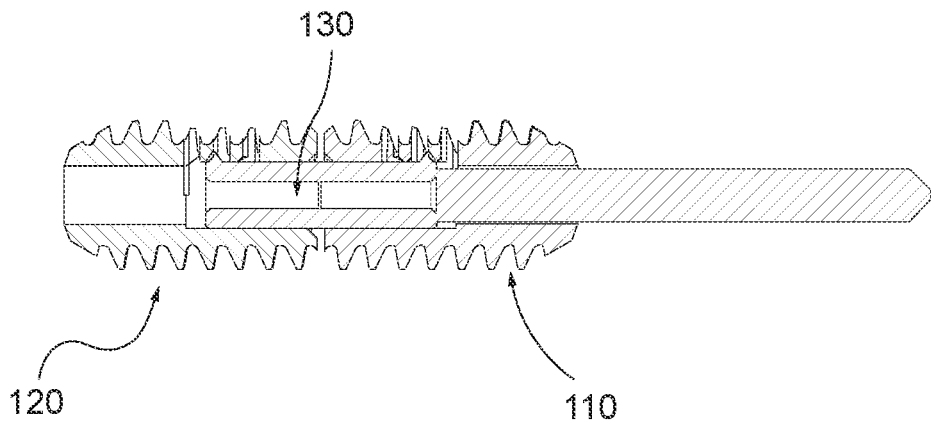
FIG. 15 is a cross-sectional side video of the bone fixation device shown in FIG. 14.
Figure 16:
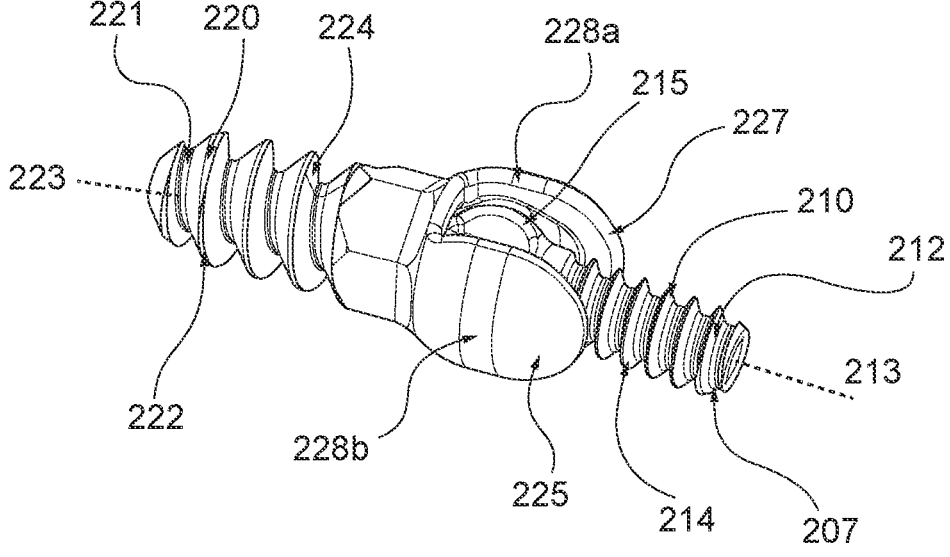
FIG. 16 is a perspective view of a bone fixation device in accordance with an exemplary embodiment of the present disclosure.
Figure 17:
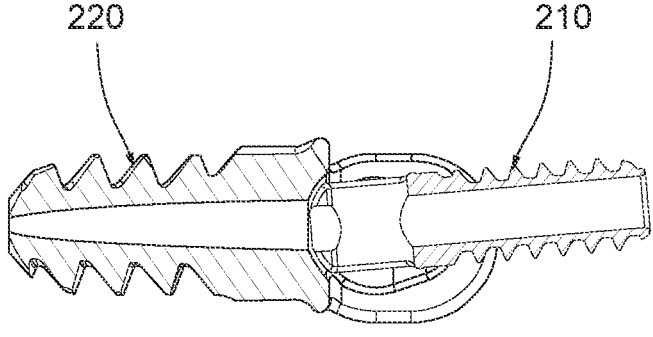
FIG. 17 is a cross-sectional side view of the bone fixation device shown in FIG. 16.
Figure 18:
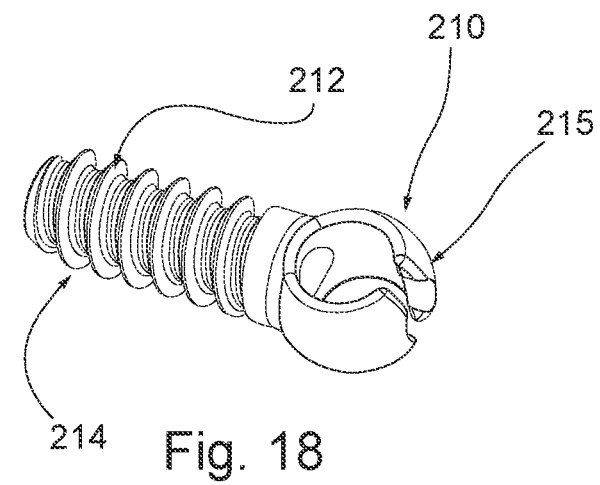
FIG. 18 is a perspective view of a first bone anchor of the bone fixation device shown in FIGS. 16-17.
Figure 19:
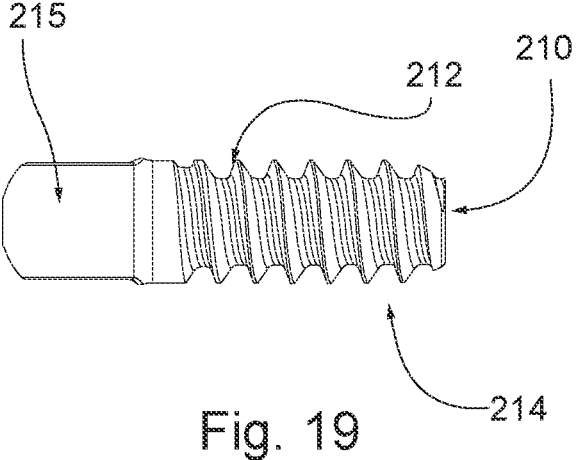
FIG. 19 is a side view of the first bone anchor shown in FIG. 18.
Figure 20:
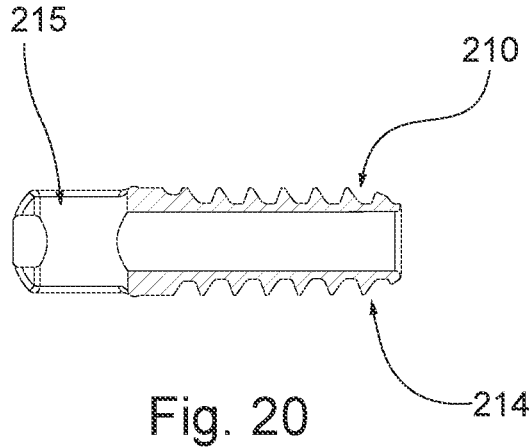
FIG. 20 is a cross-sectional side view of the first bone anchor shown in FIGS. 18-19.
Figures 21, 22, 23:
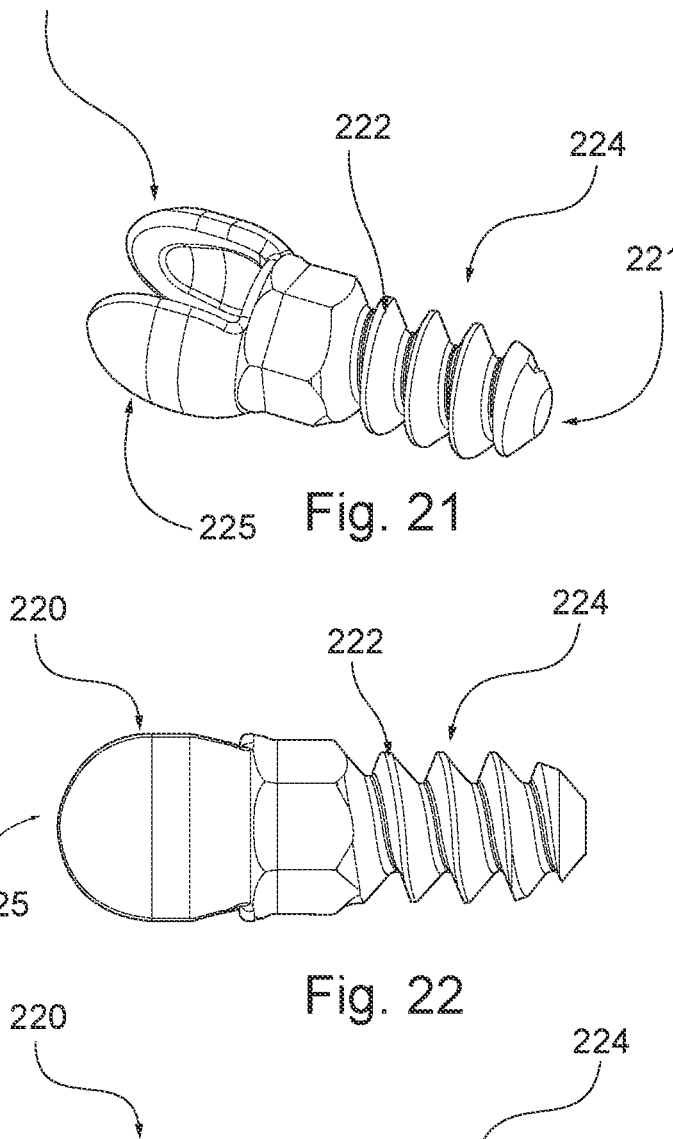
FIG. 21 is a perspective view of a second bone anchor of the bone fixation device shown in FIGS. 16-17.
FIG. 22 is a side view of the second bone anchor shown in FIG. 21.
FIG. 23 is a cross-sectional side view of the first bone anchor shown in FIGS. 21-22.
Figure 24:
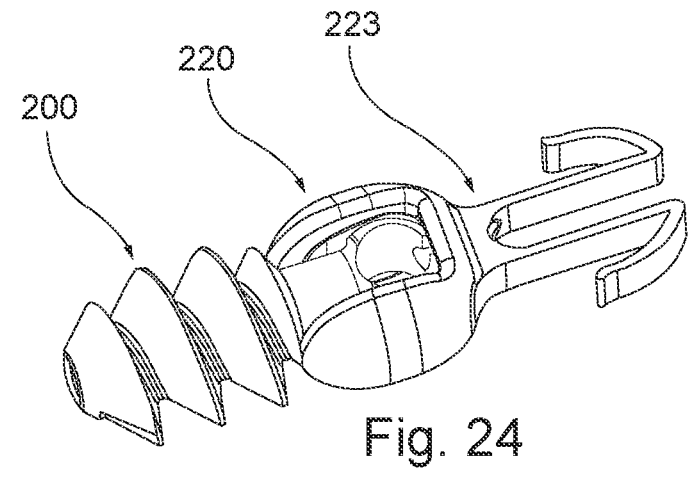
FIG. 24 is a perspective view of a bone fixation device shown in FIGS. 16-23 in accordance with an exemplary embodiment of the present disclosure.
Figure 25A:
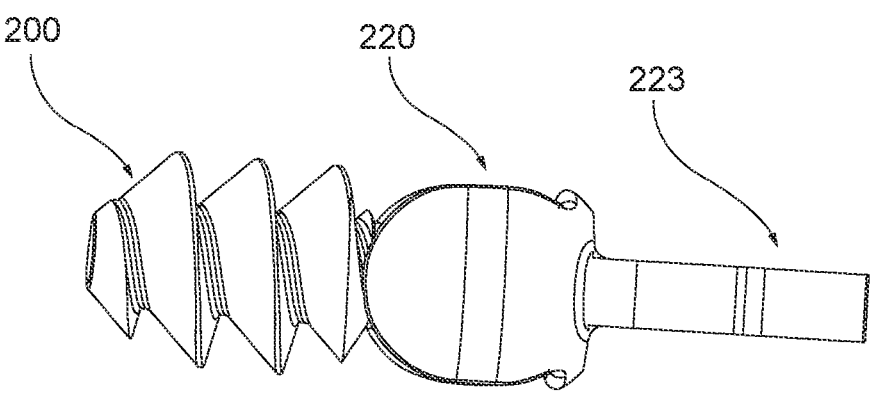
FIG. 25A is a side view of the bone fixation device shown in FIG. 24.
Figure 25B:
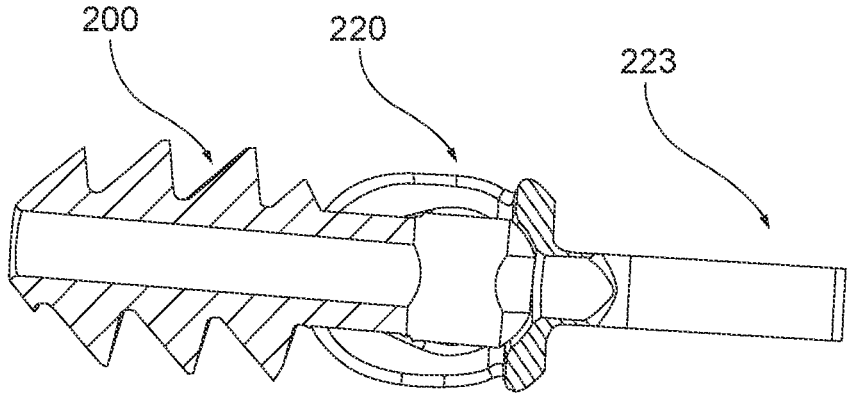
FIG. 25B is a cross-sectional side view of a first bone anchor of the bone fixation device shown in FIGS. 24-25A.
Figures 26, 27, 28:
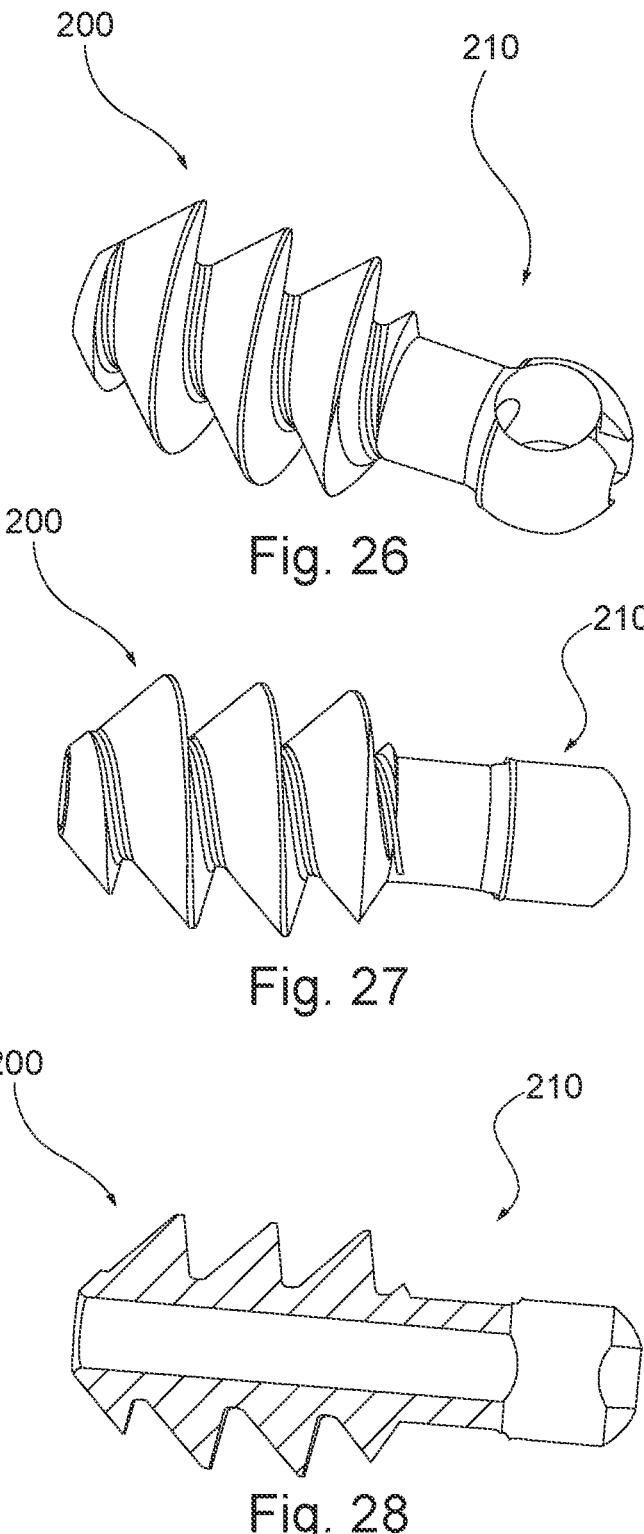
FIG. 26 is a perspective view of a first bone anchor of the bone fixation device shown in FIGS. 24-25B.
FIG. 27 is a side view of the first bone anchor shown in FIG. 26.
FIG. 28 is a cross-sectional side view of the first bone anchor shown in FIGS. 26-27.
Figure 29:
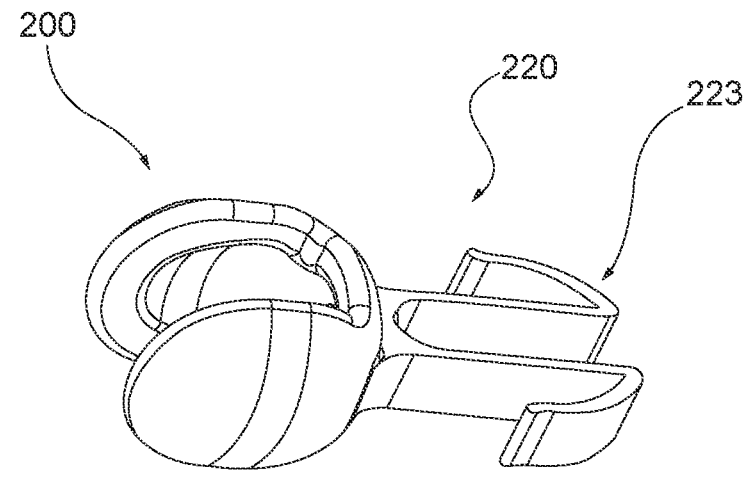
FIG. 29 is a perspective view of a second bone anchor of the bone fixation device shown in FIGS. 24-25B.
Figure 30A:
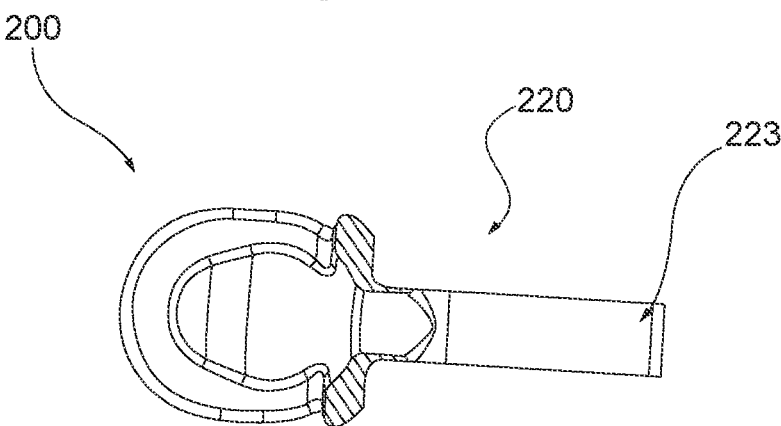
FIG. 30A is a side view of the second bone anchor shown in FIG. 29.
Figure 30B:
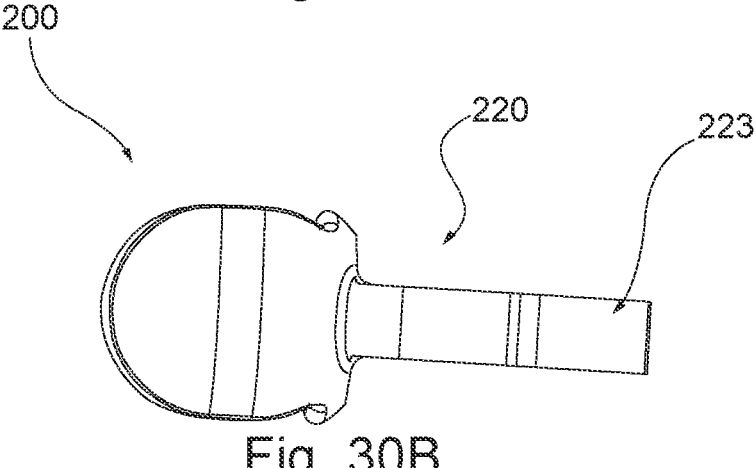
FIG. 30B is a cross-sectional side view of the first bone anchor shown in FIGS. 29-30A.

As shown in FIG. 9, when the first segment and second segment 130a, 130b are engaged with the connector element 130, the first longitudinal axis 113 and the second longitudinal axis 123 can define an angle α of about 15 degrees, but can alternatively be less than or greater than 15 degrees e.g., 13 or 17 degrees. While the first segment 130a and second segment 130b have a substantially similar length, it is to be understood that the lengths of the first segment 130a and second segment 130b may vary based on surgeon preference or the desired implant design. For example, certain bone anchors may vary in length based on the specific set of adjacent bones being fixated. Similarly, it is to be understood that the first bone anchor 110 can have a length greater than a length of the second bone anchor 120 and vice versa.

Figure 8:
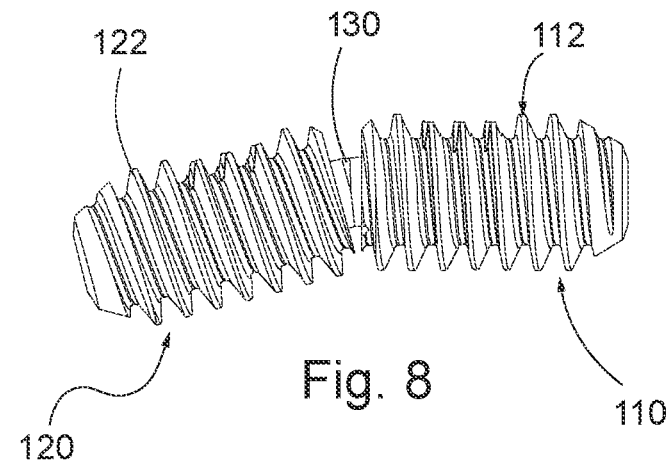
FIG. 8 is a side view of the bone fixation device shown in FIG. 7.

As shown in FIGS. 12-15, the first and second bone anchors 110, 120 can be of variable length to accommodate patient anatomy and/or surgeon preference. Similarly, the connector element 130 can be adjustably positioned along a common axis of the first and second bone anchors 110, 120 based on user preference. As shown in FIGS. 8 and 9, a portion of the connector element 130 is located outside of the first and second channels 111, 121 when the connector element 130 is matingly engaged with the first and second anchoring elements after implantation.

In operation, prior to implantation of the bone fixation device, the surgeon or operating room personnel identify the desired adjacent bones to be fused in a patient. Thereafter, the respective surface of each bone is prepared for receipt of the first and second bone anchors of the fixation device. Specifically, each bone surface is cut, burred, or drilled to prepare a bore for receipt of the respective anchoring elements. For example, the surgeon may drill a hole into a bone at or near a joint repair site for implanting the bone anchors 110, 120. The surgeon can use a driving tool to implant the first bone anchor 110 into a first bore of a first bone and the second bone anchor 120 into a second bore of a second bone adjacent the first bone such that the respective bone anchors 110, 120 are secured to the respective bones. The surgeon can implant the first and second bone anchors 110, 120 into the respective bones via any surgical equipment using techniques known to those of ordinary skill in the art.

The first bone anchor 110 and second bone anchor 120 can be of a desired size, length and diameter based on surgeon preference and the identified bone the anchoring element is being secured to. Further to this, the first bone anchor 110 and second bone anchor 120 can be of different sizes to accommodate variable sized bones in a patient. After the first and second bone anchors 110, 120 are secured in position, the connector element 130 is inserted between the respective first and second bone anchors 110, 120. Similar to the first and second bone anchors 110, 120, the connector element 130 can be of a desired size, length, shape and diameter to achieve a desired orientation of the first bone relative to the second bone. For example, the specific connector element can be tailored to a desired distance, rotation and angulation of the respective bones at the desired bone fixation site.

The process of inserting the connector element 130 can be repeated during an operation until a desired configuration for an optimal patient outcome is identified. It is to be understood that various surgical instruments known in the art can be used to implant and position the components of the fixation device inside a patient during an operation.

Following implantation of the first bone anchor 110, second bone anchor 120 and connector element 130 in a desired configuration, the connector element 130 is secured to the first and second bone anchor 110, 120 in a fixed position. Specifically, a compression force is applied to the first and second bones to lock the connector element 130 in a fixed position with the first and second bone anchors 110, 120. As a result, the first bone and second bone are secured together in a fixed orientation to facilitate bone fusion and healing.

Referring now to FIGS. 16-30B, there is shown a bone fixation device 200 in accordance with another exemplary embodiment of the present disclosure. As shown in FIGS. 16-30B, the bone fixation device 200 includes a first bone anchor 210 and a second bone anchor 220. The first bone anchor 210 is elongated along a first longitudinal axis 213. The first bone anchor is configured for securing to a distal bone. Similarly, the second bone anchor 220 is elongated along a second longitudinal axis 223. The second bone anchor 220 is configured for securing to a proximal bone. As further discussed below, the first bone anchor 210 includes a ball screw 215 and the second bone anchor 220 includes a socket portion 225 operatively connected to the ball screw 215. Specifically, the ball screw 215 is configured to be rotatably seated within the socket portion 225.

As shown in FIGS. 16-20, the first bone anchor 210 includes an elongated body 214 and a ball screw 215 extending from the elongated body. The elongated body 214 has a circular cross section, however the elongated body 214 can have any shape cross section such as hexagonal, polygonal or any other shape suitable for its intended purpose.

The elongated body 214 includes a first outer thread portion 212 for threadedly securing the first bone anchor 210 to the distal bone. Specifically, the first outer thread portion 212 is sized and shaped to be threadedly engaged within a bone canal or bore drilled into the distal bone prior to implantation of the first bone anchor 210. It is contemplated that the elongated body 214 can include a tapering frusto-conical shaped tip 207 to facilitate its attachment to the distal bone.

The ball screw 215 preferably includes an articulating surface of a suitable shape, including, but not limited to, a spherical, oval, cylindrical, or ellipsoidal shape, and permitting a predetermined movement of the ball screw 215 when rotatably seated within the socket portion 225. That is, the ball screw 215 is configured to freely rotate a predetermined amount about an axis of rotation respective to the socket portion 225. The ball screw 215 is substantially bulbous-shaped.

Similar to the first bone anchor 210, as shown in FIGS. 16 and 21-23, the second bone anchor 220 includes an elongated body 224 and the socket portion 225 extends from the elongated body. The elongated body 224 has a circular cross section, however the elongated body 224 can have any shape cross section such as hexagonal, polygonal or any other shape suitable for its intended purpose.

The elongated body 224 includes a second outer thread portion 222 for threadedly securing the second bone anchor 220 to the proximal bone. Specifically, the second outer thread portion 222 is sized and shaped to be threadedly engaged within a bone canal or bore drilled into the proximal bone prior to implantation of the second bone anchor 220. It is contemplated that the elongated body 224 can include a tapering frustoconical shaped tip 221 to facilitate its attachment to the proximal bone.

The socket portion 225 preferably includes a corresponding articulating surface to the articulating surface of the ball screw 215. The corresponding articulating surface of the socket portion 225 is of a suitable shape such as, for example, a spherical, oval, cylindrical, or ellipsoidal shape. As discussed above, when operatively connected, the ball screw 215 is configured to rotatably sit within the socket portion 225. The socket portion 225 is substantially U-shaped.

The socket portion 225 includes a proximally facing opening 227 for receiving the ball screw 215 and a pair of diametrically opposing curved walls 228a, 228b for adjustably retaining the ball screw 215. As such, the ball screw 215 is smaller in diameter on average than a diameter of the socket portion 225.

Similar to the bone fixation device 100 of the previously discussed embodiment, the first bone anchor 210 and the second bone anchor 220 of the bone fixation device 200 are implanted into the respective distal bone and proximal bone. Thereafter, the ball screw 215 is rotatably seated in the socket portion 225. As a result, movement of the ball screw 215 within the socket portion 225 allows for translational and rotational movement of the distal bone relative to the proximal bone. The ball screw 215 is rotated within the socket portion 225 until a desired orientation of the distal bone relative to the proximal bone is achieved.

In accordance with another aspect of the exemplary embodiment, the bone fixation device includes a compression member (not shown) received within a recess of the socket portion 225. The compression member is configured to apply a biasing force for securing the ball screw 215 and socket portion 225 into a fixed position. The biasing force causes the ball screw 215 to radially expand outwardly within the socket portion 225, thereby drawing the first and second bone anchors 210, 220 closer to one another and resulting in bone compression.

Referring now to FIGS. 24-30B, in accordance with another aspect of the exemplary embodiment, the second bone anchor 220 includes a fastener 223 for securing the second bone anchor 220 to the proximal bone. For example, the fastener 223 can be a pair of prongs. Other structures and mechanical components in addition to the one illustrated here can perform the function of securing the component to the bones. These can include differently shaped prongs, flexible links or any other type of fastener.

Referring now to FIGS. 31-37, there is shown a bone fixation device 300 in accordance with another exemplary embodiment of the present disclosure. The bone fixation device 300 includes a first bone anchor 310 and a second bone anchor 320. The first bone anchor 310 is elongated along a first longitudinal axis 313 for securing to a distal bone. Similarly, the second bone anchor 320 is elongated along a second longitudinal axis 323 for securing to a proximal bone. As further discussed below, the first bone anchor 310 includes a ball screw 315 and the second bone anchor 320 includes a socket portion 325 operatively connected to the ball screw 315. Specifically, the ball screw 315 is configured to be received within the socket portion 325.

As shown in FIGS. 31-34, the first bone anchor 310 includes an elongated body 314 and a ball screw 315 extending from the elongated body 314. The elongated body 314 has a circular cross section, however the elongated body 314 can have any shape cross section such as hexagonal, polygonal or any other shape suitable for its intended purpose.

The elongated body 314 includes a first outer thread portion 312 for threadedly securing the first bone anchor 310 to the distal bone. Specifically, the first outer thread portion 312 is sized and shaped to be threadedly engaged within a bone canal or bore drilled into the distal bone prior to implantation of the first bone anchor 310. It is contemplated that the elongated body 314 can include a tapering frustoconical shaped tip 307 to facilitate its attachment to the distal bone. As discussed below, the ball screw 315 is configured to freely rotate within a recess 327 of the socket portion 325.

Similar to the first bone anchor 310, as shown in FIGS. 31, 32, 35 and 36, the second bone anchor 320 includes an elongated body 324 and the socket portion 325 extends from the elongated body 324. The elongated body 324 has a circular cross section, however the elongated body 324 can have any shape cross section such as hexagonal, polygonal or any other shape suitable for its intended purpose.

The elongated body 324 includes a second outer thread portion 322 for threadedly securing the second bone anchor 320 to the proximal bone. Specifically, the second outer thread portion 322 is sized and shaped to be threadedly engaged within a bone canal or bore drilled into the proximal bone prior to implantation of the second bone anchor 320. It is contemplated that the elongated body 324 can include a tapering frustoconical shaped tip 321 to facilitate its attachment to the proximal bone.

The recess 327 of the socket portion 325 is substantially U-shaped. When operatively connected, the ball screw 315 is configured to be rotatably adjustable within the socket portion 325. Similar to the bone fixation device 200 of the previously discussed embodiment, the ball screw 315 is rotated within the socket portion 325 until a desired orientation of the distal bone relative to the proximal bone is achieved.

Figure 31:
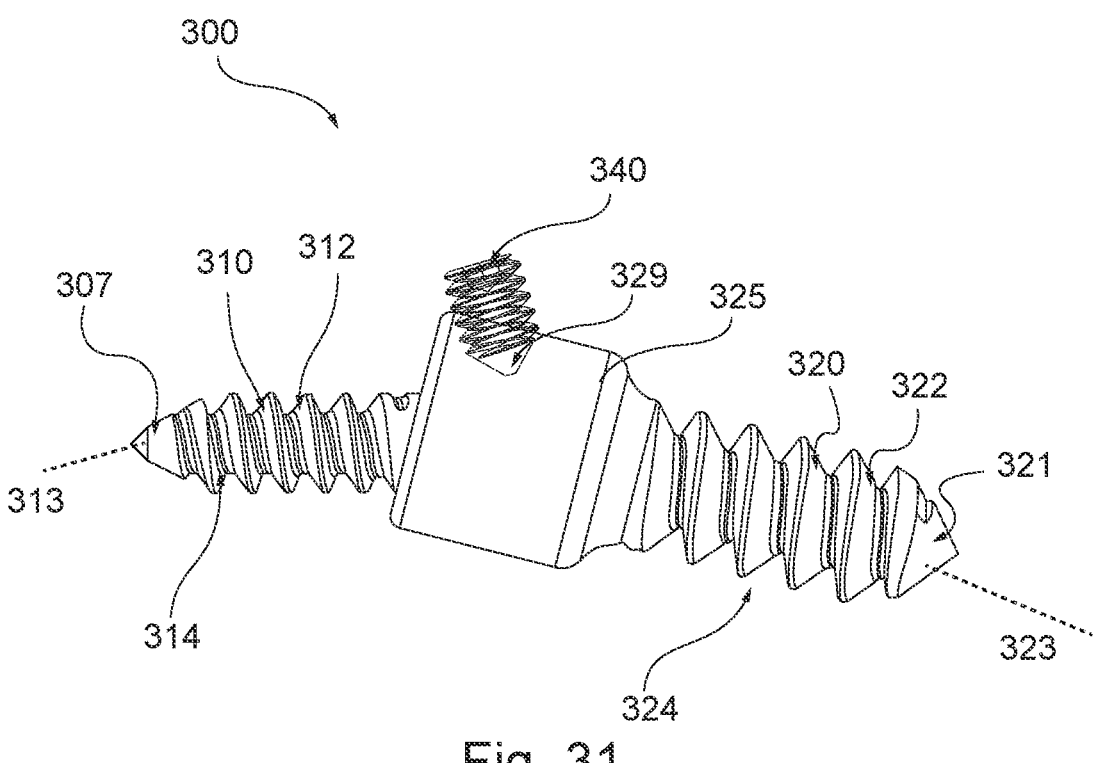
FIG. 31 is a perspective view of a bone fixation device in accordance with an exemplary embodiment of the present disclosure.
Figure 32:
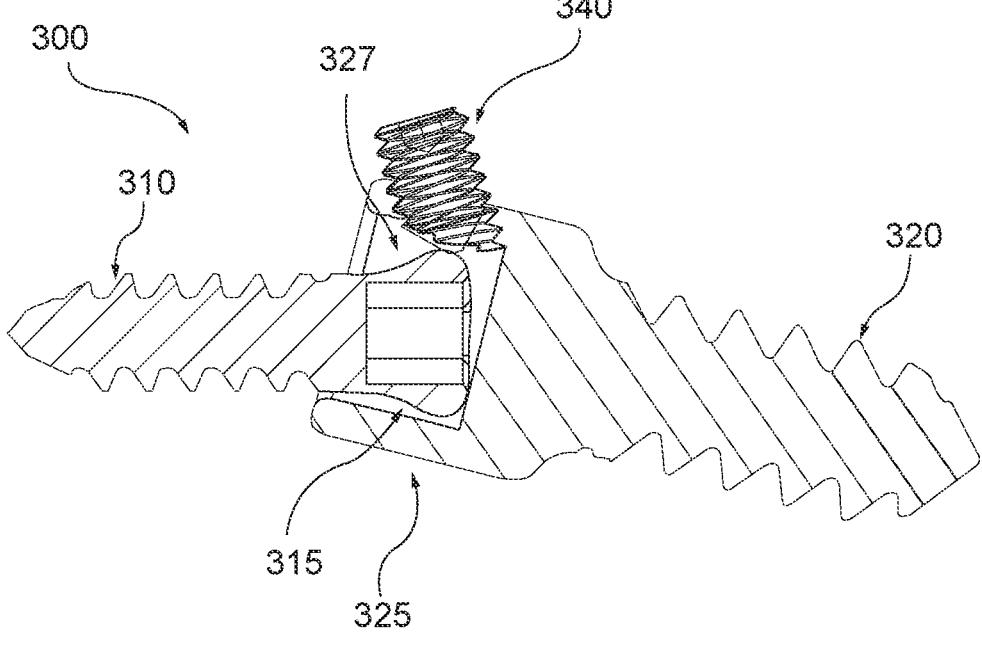
FIG. 32 is a cross-sectional perspective view of the bone fixation device shown in FIG. 31.

The socket portion 325 further includes a threaded bore 329 extending therethrough and in communication with the recess 327. Upon positioning of the ball screw 315 within the socket portion 325 at a desired orientation, a compression member 340 is threadedly received within the threaded bore 329. Specifically, as shown in FIGS. 31 and 32, the compression member 340 biases the ball screw 315 and socket portion 325 for fixedly securing a position of the distal bone relative to the proximal bone. The compression member 340 can be a set screw.

Referring now to FIGS. 38-44B, there is shown a bone fixation device 400 in accordance with another exemplary embodiment of the present disclosure. As shown in FIGS. 38-44B, the bone fixation device 400 includes a first bone anchor 410 and a second bone anchor 420. The first bone anchor 410 is elongated along a first longitudinal axis 413 for securing to a distal bone. Similarly, the second bone anchor 420 is elongated along a second longitudinal axis 423 for securing to a proximal bone. As described below, the first bone anchor 410 and the second bone anchor 420 may include similar features and a discussion of such features are applicable to both the first and second bone anchors, unless stated otherwise.

Referring now to FIGS. 38-42B, the first bone anchor 410 is generally an elongated body having the longitudinal axis 413. The first bone anchor 410 is preferably a cylindrical member having a circular cross section. In alternative embodiments, however, the first bone anchor 410 can have any shape cross section such as hexagonal, polygonal or any other shape suitable for its intended purpose.

The first bone anchor 410 includes a first plurality of exterior threads 412 for threadedly securing the first bone anchor 410 to the distal bone and the second bone anchor 420. Specifically, the first plurality of exterior threads 412 extends along a length of the first bone anchor 410 and is sized and shaped to be threadedly engaged within a bone canal or bore drilled into the distal bone prior to implantation of the first bone anchor 410. As shown, the first bone anchor includes a threaded head portion and a threaded shaft, as shown.

Referring now to FIGS. 38-44B, the second bone anchor 420 is sized and shaped to engage the first bone anchor 410. As shown, the second bone anchor 420 is generally an elongated body having the longitudinal axis 423. The second bone anchor 420 is preferably a cylindrical member having a circular cross section but having a recessed portion. The recessed portion is positioned toward the proximal end of the second bone anchor. The recessed portion generally extends inward toward a central axis. In addition, the recessed portion is extends along a generally angled path that is angled with respect to the central axis of the anchor 420. The recessed portion is threaded. However the second bone anchor 420 can also have any shape cross section suitable for its intended purpose of securing to the proximal bone.

The second bone anchor 420 includes a second plurality of exterior threads 422 for threadedly securing the second bone anchor 420 to the proximal bone and the first bone anchor 410. Specifically, the second plurality of exterior threads 422 extends along a length of the second bone anchor 420 and is sized and shaped to be threadedly engaged within a bone canal or bore drilled into the proximal bone prior to implantation of the second bone anchor 420.

Figures 38, 39, 40:
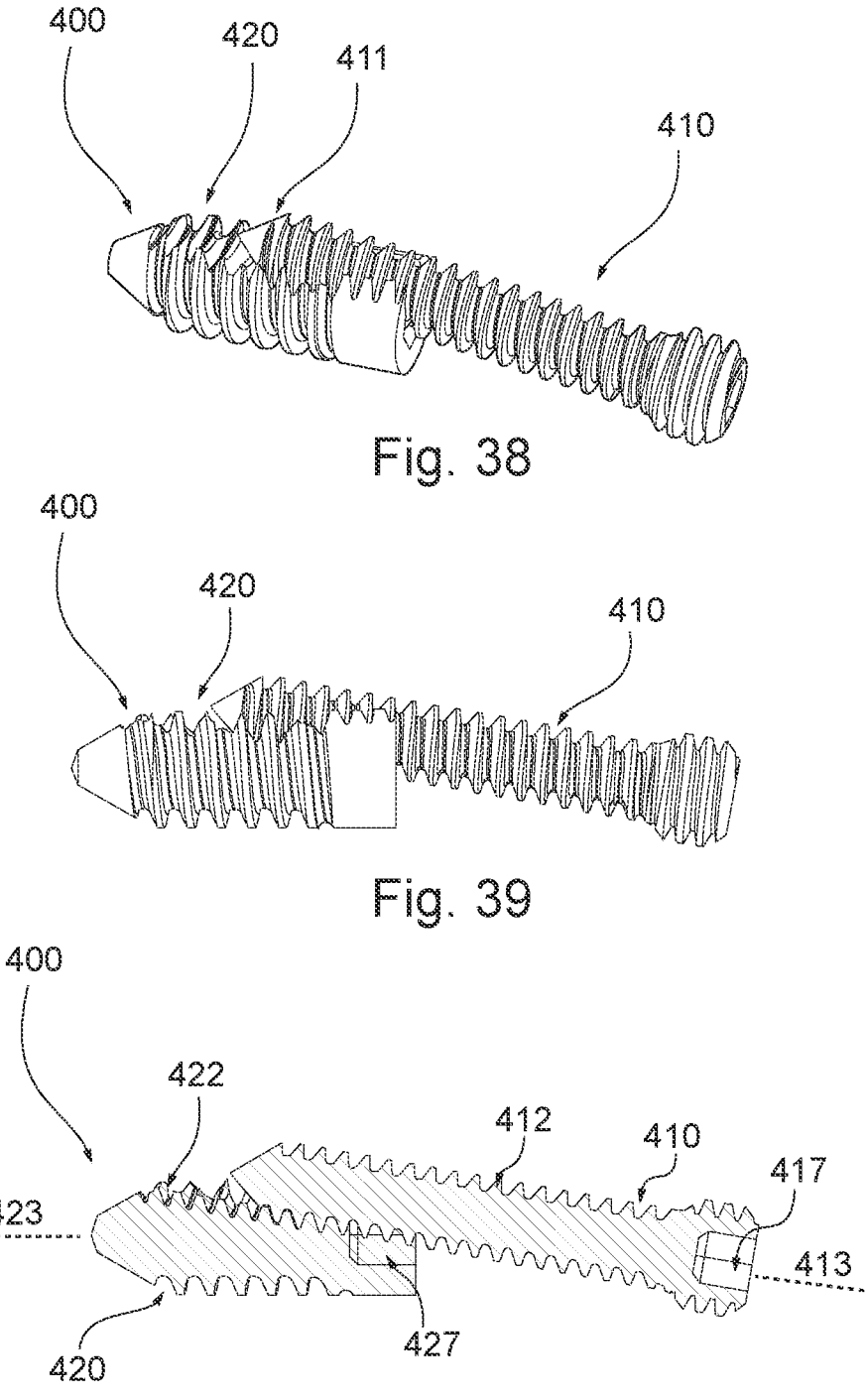
FIG. 38 is a perspective view of a bone fixation device in accordance with an exemplary embodiment of the present disclosure.
FIG. 39 is a side view of the bone fixation device shown in FIG. 38.
FIG. 40 is a cross-sectional side view of the bone fixation device shown in FIGS. 38-39.
Figure 41:
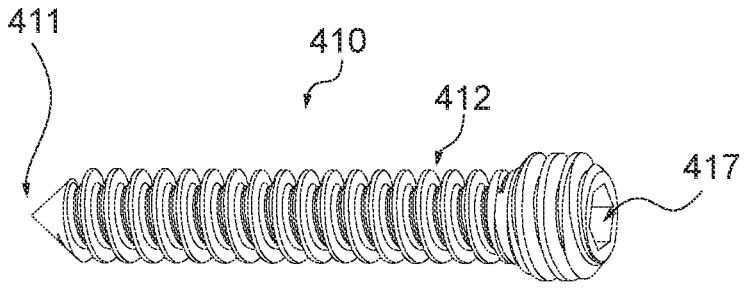
FIG. 41 is a perspective view of a first bone anchor of the bone fixation device shown in FIGS. 38-40.
Figure 42A:
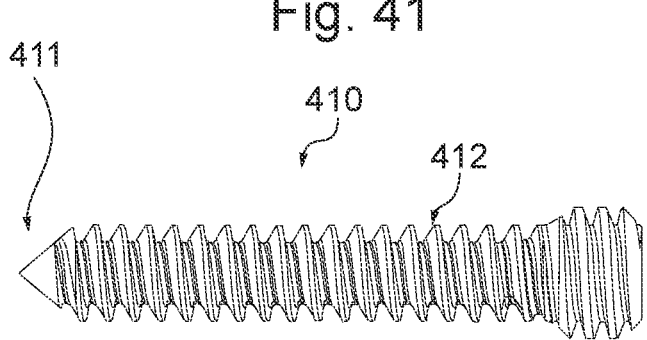
FIG. 42A is a side view of the first bone anchor shown in FIG. 41.
Figure 42B:
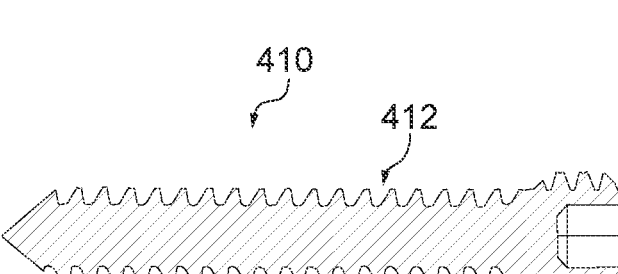
FIG. 42B is a cross-sectional side view of the first bone anchor shown in FIGS. 41-42A.
Figure 43:
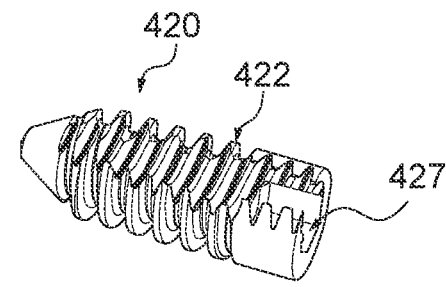
FIG. 43 is a perspective view of a second bone anchor of the bone fixation device shown in FIGS. 38-40.
Figure 44A:
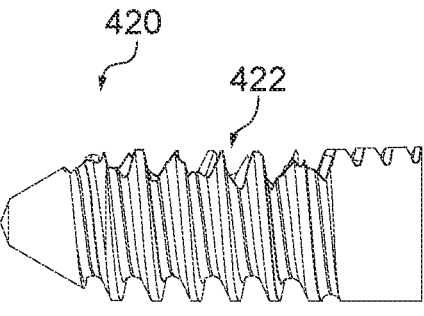
FIG. 44A is a side view of the second bone anchor shown in FIG. 43.
Figure 44B:
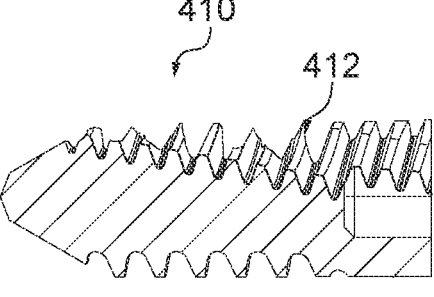
FIG. 44B is a cross-sectional side view of the second bone anchor shown in FIGS. 43-44A.

As shown in FIGS. 38-40, the first plurality of exterior threads 412 is threadedly engaged to the second plurality of exterior threads 422 for adjustably securing a position of the distal bone relative to the proximal bone. In accordance with an aspect of the exemplary embodiment, the first and second bone anchors 410, 420 are configured as screws.

It is to be understood that the first and second bone anchors 410, 420 can have any suitable size and shape. For example, the first and second bone anchors 410, 420 may have about the same diameter. Alternatively, the first bone anchor 410 may be lesser in diameter than the diameter of the second bone anchor 420. In such an aspect, the first bone anchor 410 may contain a frustoconical shaped tip 411 that is partially received within a cannulated opening 427 of the second bone anchor 420 for securing a position of the distal bone relative to the proximal bone. That is, the first bone anchor 410 and second bone anchor 420 can be of a desired size, length and diameter based on surgeon preference and the identified bone the anchoring element is being secured to. The first bone anchor 410 can also have a cannulated opening 417.

Following implantation of the first and second bone anchors 410, 420, the first bone anchor 410 is threadedly secured to the second bone anchor 420. Specifically, the first plurality of exterior threads 412 is threadedly engaged to the second plurality of exterior threads 422 to fixedly secure a position of the distal bone relative to the proximal bone to facilitate bone fusion and healing.

Referring now to FIGS. 45-50B, there is shown a bone fixation device 500 in accordance with another exemplary embodiment of the present disclosure. The bone fixation device 500 includes a first bone anchor 510 and a second bone anchor 520. The first bone anchor 510 is elongated along a first longitudinal axis 513 for securing to a distal bone. Similarly, the second bone anchor 520 is elongated along a second longitudinal axis 523 for securing to a proximal bone. As further discussed below, the first bone anchor 510 is pivotably connected to the second bone anchor 520 for adjustably securing a position of the distal bone relative to the proximal bone when implanted. Such a pivotable arrangement is achieved via a ball screw and socket portion.

Figures 45, 46A, 46B:
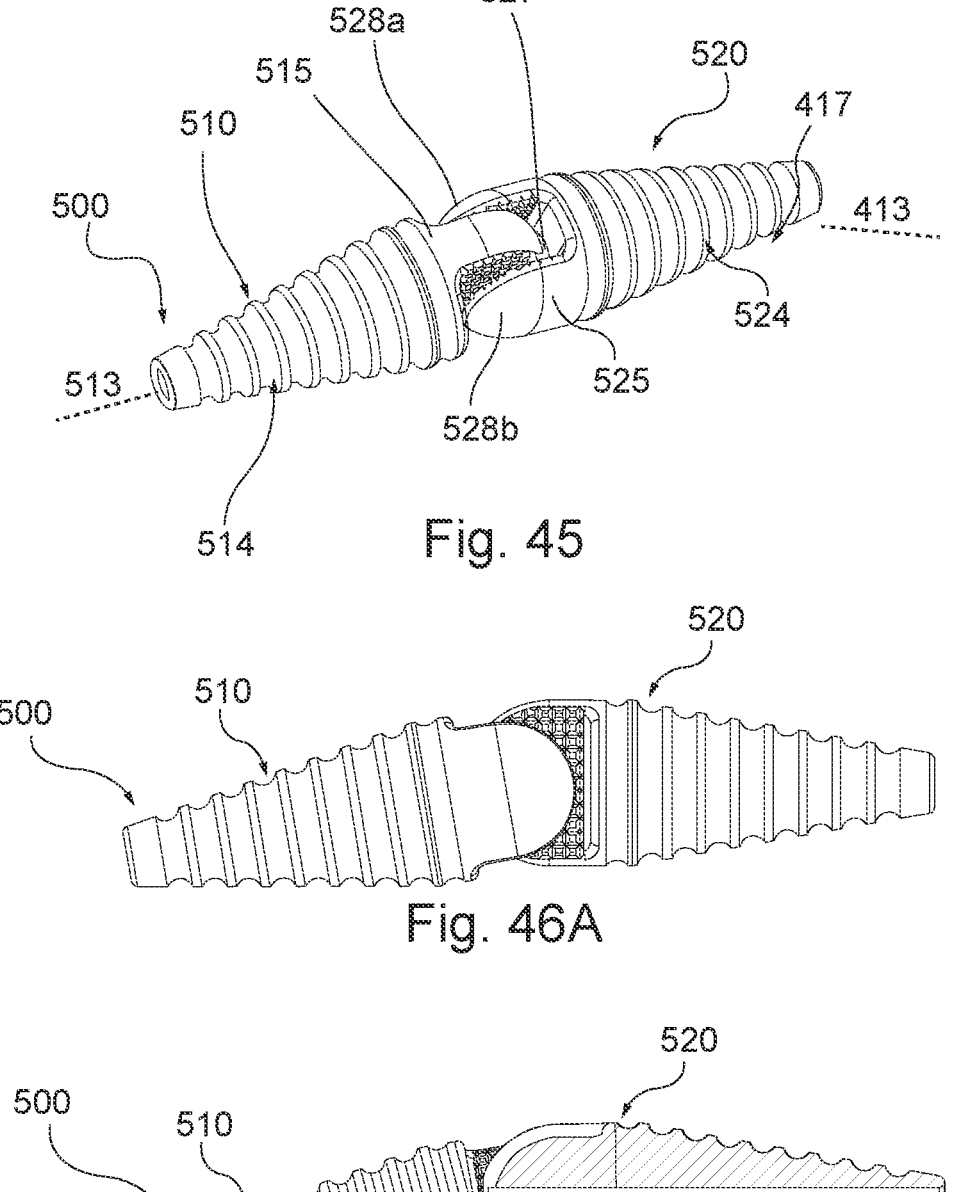
FIG. 45 is a perspective view of a bone fixation device in accordance with an exemplary embodiment of the present disclosure.
FIG. 46A is a side view of the bone fixation device shown in FIG. 45.
FIG. 46B is a cross-sectional side view of the bone fixation device shown in FIGS. 45-46A.
Figures 47, 48A, 48B:
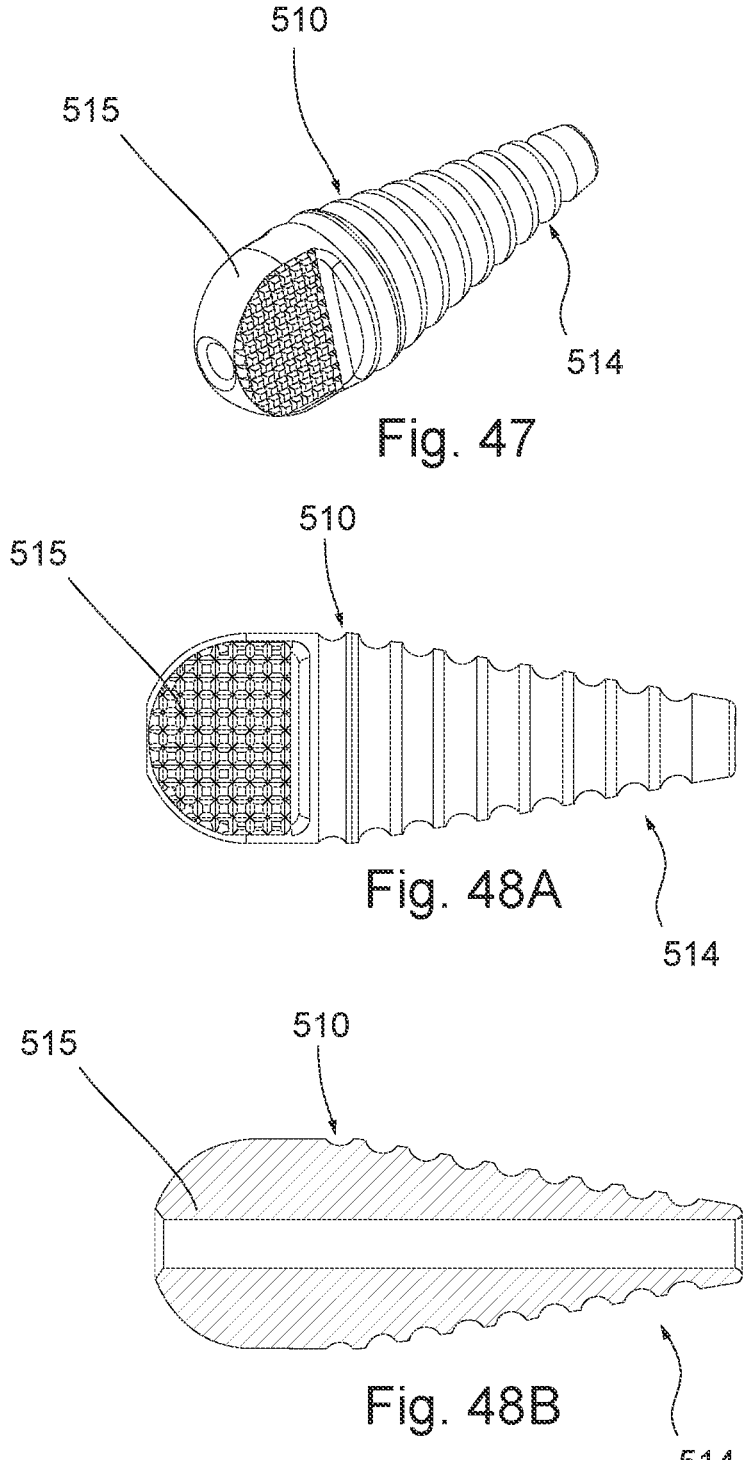
FIG. 47 is a perspective view of a first bone anchor of the bone fixation device shown in FIGS. 45-46B.
FIG. 48A is a side view of the first bone anchor shown in FIG. 47.
FIG. 48B is a cross-sectional side view of the first bone anchor shown in FIGS. 47-48A.

As shown in FIGS. 45-46B, the first bone anchor 510 includes a tapering elongated body 514 and a ball screw 515 extending from the elongated body 514. The elongated body 514 has a tapering profile to facilitate its minimally invasive implantation as well as to facilitate securing the first bone anchor 510 to the distal bone. The elongated body 514 can have an exterior thread portion for threadedly securing the first bone anchor 510 to the distal bone. The tapering elongated body 514 can be cannulated.

The ball screw 515 preferably includes an articulating surface of a suitable shape, including, but not limited to, a spherical, oval, cylindrical, or ellipsoidal shape, and configured to be received within a socket portion of the second bone anchor 520.

As shown in FIGS. 46A, 46B and 49-50B, the second bone anchor 520 includes a tapering elongated body 524 and a socket portion 525 extending from the elongated body 524. The elongated body 524 has a tapering profile to facilitate its minimally invasive implantation as well as to facilitate securing the second bone anchor 520 to the proximal bone. The elongated body 524 can have an exterior thread portion for threadedly securing the second bone anchor 520 to the proximal bone. The tapering elongated body 524 can be cannulated.

The socket portion 525 preferably includes a corresponding articulating surface to the articulating surface of the ball screw 515. The corresponding articulating surface of the socket portion 525 is of a suitable shape such as, for example, a spherical, oval, cylindrical, or ellipsoidal shape. The socket portion 525 is substantially U-shaped. As shown in FIGS. 45, 46 and 49, the socket portion 525 includes a proximally facing opening 527 for receiving the ball screw 515 and a pair of diametrically opposing curved walls 528a, 528b for adjustably retaining the ball screw 515.

Similar to the bone fixation devices 100, 200, 300 and 400 of the previously discussed embodiments, the first and second bone anchors 510, 520 of the bone fixation device 500 are implanted into the distal and proximal bones. Thereafter, the ball screw 515 is pivotably connected to the socket portion 525 for pivotably rotating the first bone anchor 510 relative to the second bone anchor 520. In order to facilitate a minimally invasive procedure for implantation, the first and second bone anchors 510, 520 are movable between a collapsed position and an expanded position.

In operation, once the desired orientation of the distal bone relative to the proximal bone is achieved, the bone fixation device 500 includes a tensioning tool (not shown) configured to apply a compression force to the ball screw 515 and socket portion 525 for fixedly securing a position of the distal bone relative to the proximal bone. The tensioning tool is a crimping mechanism.

Referring now to FIGS. 51-57, there is shown a surgical instrument 600 for coupling one or more bone segments together in accordance with an exemplary embodiment of the present disclosure. As shown in FIGS. 51-57, the surgical instrument 600 includes a curved elongated body 614 having a first end 608 and a second end 612 opposite the first end 608. The surgical instrument 600 further includes a first positioning element 610 adjustably mounted to the first end 608 of the elongated body 614 and a second positioning element 620 adjustably mounted to the second end 612 of the elongated body 614. During implantation, the first positioning element 610 is positioned at a desired joint location and the second positioning element 620 is positioned adjacent a tip of a distal bone spaced from the desired joint location.

As shown in FIG. 52, the surgical instrument further includes a guide wire 624 that is elongated along a longitudinal axis 628, wherein the guide wire 624 includes a proximal end portion 630 and a distal end portion 632 spaced from the proximal end portion 630 along the longitudinal axis 628. The proximal end 630 is configured to be received within the first positioning element 610 and the distal end 632 is configured to be received within the second positioning element 620 for facilitating fusion of one or more adjacent bone segments.

The surgical instrument 600 can be manufactured from a number of materials including nitinol, titanium alloys, non-titanium alloys, or other polymeric materials, e.g., plastics, plastic composites, polyetheretherketone (PEEK), and ceramics such as silicon nitride, zirconium oxide, silver oxide, and other suitable materials for facilitating detachment of the surgical instrument 600 after implantation of the guide wire 624.

The first positioning element 610 is substantially U-shaped (FIG. 52) for facilitating removal of the surgical instrument 600. The first positioning element 610 can also be substantially conical to facilitate positioning of the surgical instrument 600 and guide wire 624 during implantation. In accordance with yet another aspect, the first positioning element 610 can be substantially barb-shaped to facilitate positioning of the surgical instrument 600 and guide wire 624 during implantation.

As shown in FIGS. 60-63, the first positioning element 610 can include a flange member 636 to facilitate positioning of the surgical instrument 600. Specifically, the flange member 636 facilitates stability of the surgical instrument 600 position during implantation of the guide wire 624.

It is to be understood that the elongated body 614 can be formed with a plurality of segmented portions having different cross-sectional diameters to facilitate implantation of a guide wire 624 and removal of the surgical instrument 600 subsequently thereafter.

In operation, a surgeon identifies the desired joint to be fused. Thereafter, the surgical instrument 600 is inserted at the desired joint location through incisions made at the surface of the skin of a patient. Specifically, the first positioning element 610 is placed in the tip of the toad and the second positioning element 620 (e.g. a cannula) is placed in the desired joint. The instrument 600 includes a flange at the tip near 620 that sits on the patient's skin and thus locates the cannula of 620 for the surgeon.

It is to be understood that this procedure and surgical instrument 600 is not limited to any one area of use in the body of a patient. Once the surgical instrument 600 is positioned, the guide wire 624 is driven from the second positioning element 620 to the first positioning element 610. Once the guide wire 624 is operatively secured through the desired bone segments, the surgical instrument 600 can be removed, leaving the guide wire 624 in place for facilitating fusion of the bone segments.

Referring now to FIGS. 64-66, there is shown a surgical instrument 700 for preparing one or more bone segments of a joint for fusion. Specifically, the surgical instrument 700 is designed to prepare a joint for fusion in a minimally invasive fashion in coordination with the use of the surgical instrument 700 described above.

The surgical instrument 700 includes an elongated shaft 714, an end portion 710 about a first end 708 of the elongated shaft 714 for securing to a rotating instrument (not shown), a surgical cutting tool 720 about a second end 712 of the elongated shaft 714 opposite the first end 712, and a flange member 715 positioned along the elongated shaft 714 between the end portion and the surgical cutting tool.

In accordance with an aspect of the exemplary embodiment, the surgical cutting tool 720 is a burr. In accordance with another aspect, the surgical cutting tool 720 further includes a rounded tip 721 for preventing soft tissue damage during preparation of a joint.

In operation, the flange member 715 prevents over plunging of the surgical instrument 700 into a desired joint when a surgical cutting tool such as a burr is being used to prepare a desired joint for implantation of a guide wire.

Another embodiment of a bone fixation system configured to fuse one or more bone segments together and shown in FIGS. 67 through 73. The bone fixation system includes a bone fixation device 800, which includes at least a first bone anchor 810 and a second bone anchor 820, and surgical tools use to facilitate implantation of the bone fixation device 800 in place. The bone fixation device 800 may be similar to one or more of the bone fixation devices described above and illustrated in FIGS. 1 through 50B. As shown, typically, the first bone anchor 810 is implanted in place, and the second bone anchor 820 is then implanted to engage the first bone anchor 810 and provide a reliable and flexible mechanism to fix bone segments in a desired position. The first bone anchor may be referred to as a proximal bone anchor and the second bone anchor may be referred to as a distal bone anchor.

The first bone anchor 810 includes a head 814 and a shaft 824 that extends from the head 814 along a bone anchor axis 813. In the embodiment shown, an entirety of the head 814 and the shaft 824 is threaded. However, less than all of the head 814 and shaft 824 may be threaded as need. The head 814, may be conical, include spherical portion, or be cylindrical. As shown, each thread has a distal side 828, a proximal side 832, and an outward surface 836 that connects the distal side 828 to the proximal side 832. The outward surface 836 is substantially parallel to the first bone anchor axis 813, the distal side 828 is angled with respect to the bone anchor axis 813, and the proximal side 832 is angled with respect to the first bone anchor axis 813 and the distal side 828. In this regard, the first bone anchor 810 includes what may be referred to as buttress threads.

The cross-sectional dimension of the first bone anchor 810 varies along its length. More specifically, the head 814 and a proximal portion of the shaft 824 have a first cross-sectional dimension D4, and a distal portion of the shaft 824 has a second cross-sectional dimension D5 that is smaller than the first cross-sectional dimension D4. In other embodiments, such as bone anchors described elsewhere in the present application, the head 814 has a first cross-sectional dimension D4, and an entirety of the shaft 824 has a second cross-sectional dimension D5 that is smaller than the first cross-sectional dimension D4.

The head 814 includes an inner surface 840 defining mating features for engagement with a driving tool and a leading end of the surgical instrument. More specifically, the first positioning element 610 is configured to adjustably engage the head 814 of the first bone anchor 810, as needed.

The second or distal bone anchor 820 has a head 844 and a shaft 848 that extends from the head 844 along a bone anchor axis 823. As shown, the shaft 848 has a proximal portion 852 that is distal to the head 844, and a distal portion 856 that is distal to the proximal portion 852. The distal portion defines a distal end of the second bone anchor 820 while the head 844 defines a proximal end of the second bone anchor 820. In the embodiment shown, a portion of the shaft 848 is not threaded. More specifically, an entirety of the head 844 and a distal portion of the shaft 848 is threaded while the proximal portion of the shaft 848 is unthreaded. In one example, such as that shown in figures, the proximal portion comprises up to one-half of a length of the shaft 848.

When the first bone anchor 810 and the second bone anchor 820 is implanted in first bone segments and second bone segments, respectively, a distal most tip of the first bone anchor 810 is positioned proximate or directly in contact with the head 844 of the second bone anchor 820.

As shown in FIGS. 74 and through 77, a first surgical tool 900 may be considered a guide or a drill guide and may be used to help align the insertion path of the second bone anchor with the first bone anchor. As illustrated, the surgical instrument 900 has an elongated body 914 with a first leg 908 having a leading end, a second leg 912 having a trailing end spaced from the leading end along and aligned with an alignment axis 924, and a brace 915 that connects the first leg 908 to the second leg 912. The entirety of the brace 915 is spaced apart and does not intersect the alignment axis 924. In this manner, the elongated body 914 may have a generally U-shaped configuration although the shape is not limited strictly to a U-shape.

The surgical tool 900 includes a first positioning element 910 and a second positioning element 920 that is generally aligned with the first positioning element 910 along and with an alignment axis 924. More specifically, the first positioning element 910 is coupled to the leading end 908 of the elongated body 914 and the second positioning element 920 is coupled to the trailing end 912 of the elongated body 914. The first positioning element 910 is configured to be positioned at a desired joint location so that the second positioning element 920 can be positioned adjacent a tip of a bone spaced from the desired joint location along the alignment axis 924. In this way, the surgical tool 900 provides a means to insert other fixation or medical devices, such as a K-wire, guide wire, or surgical pin, through positioning elements and helps define an insertion path for the second bone anchor.

As shown in FIG. 76, the first positioning element 910 has a forward end 928, a rearward end 932 spaced from the forward end 928, an outer wall 936 that extends from the forward end 928 to the rearward end 932, and a first channel 940 that extends from the forward end 928 to the rearward end 932 along the alignment axis 924. In FIGS. 74-77, the forward end 928 is tapered to engage a proximal end of a bone anchor and the first channel 940 is configured to receive the wire therethrough. The first positioning element 910 has a first length that extends from the forward end 928 to the rearward end 932.

In addition, the second positioning element 920 has a forward end 944, a rearward end 948 spaced from the forward end 944, an outer wall 950 that extends from the forward end 944 to the rearward end 948, and a second channel 952 that extends from its forward end 944 to its rearward end 948 along the alignment axis 924. The second channel 952 is also configured to receive the wire therethrough. The second positioning element 920 has a second length that extends from its forward end 944 to its rearward end 948, wherein the second length is greater than the first length. In general, the second length is between 1.5 and 3.0 times as long as the first length of the first positioning element 910. This added length provides a more stable path to insert a wire or the like, while the shortened length of the first positioning element 910 helps provide needed adjustability in use so that proper alignment between the proximal end of the bone anchor and second positioning element 920 can be attained.

The first and second positioning elements 910, 920 are spaced apart a certain distance along the alignment axis 924. More specifically, the rearward end 932 of the first positioning element 910 and the forward end 944 of the second positioning element 920 is spaced apart a distance that is aligned along the alignment axis 924. The distance between the first and second positioning element 910, 920 along the alignment axis 924 is substantially unobstructed. This creates some space for the tissue to be manipulated as needed while still maintaining the desired alignment.

The first positioning element 910 may have a number of configurations to facilitate adjustable engagement with the first bone anchor. In several examples, the outer wall 936 of the first positioning element 910 includes a curved surface that curves around the alignment axis 924. This configuration can define a generally cylindrical body. The forward end 928 may further define a forward tip of the forward end 928 of the first positioning element 910 that is tapered.

In another example, such as that shown in FIG. 74, the outer wall 936 of the first positioning element 910 includes an engagement head for mating engagement with a head of a first bone anchor. In such an example, the outer wall 936 of the first positioning element 910 includes angled surfaces for mating with a head of a first bone anchor. The first positioning element 910 also includes a ramp at the rearward end 932. The ramp is angled to the rearward end, creating space to manipulate the orientation of the first positioning element 910 relative to first bone anchor. In yet another example, the outer wall 936 of the first positioning element 910 extends partially around the alignment axis 924 such that the first channel 940 is open along one side thereof.

In an example as shown in FIGS. 74, 75, and 77, the second positioning element 920 extends partially around the alignment axis 924 such that the second channel 952 is open along one side thereof. In other configurations, however, the second position element 920 extends around the alignment axis 924.

Another embodiment of a surgical tool 1000 shown in FIGS. 78-81 includes an elongated body 1014 with a first leg 1008, a second leg 1012, and a brace 1015 that connects the first leg 1008 to the second leg 1012. Like embodiments described above, the entirety of the brace 1015 is spaced apart and does not intersect the alignment axis 1024. In the embodiment shown, the first positioning element 1010 is a curved member coupled to the first leg 1008 of the elongated body, the second positioning element 1020 is coupled to the second leg 1012 and includes a body 1028 with a channel 1032 that extends therethrough. Furthermore, the alignment axis 1024 passes through a center of the ring member and second positioning element 1020.

The ring member 1010 includes an outer ring wall 1036 that extends around the alignment axis. The outer ring wall 1036 includes an outer surface 1040, and inner surface 1044 opposite the outer surface 1040 and that faces the alignment axis 1024, the inner surface 1044 defining a substantial opening sized to receive a digit therethrough. In this manner, the ring wall can surround a toe or other digit. The outer ring wall 1036 includes a plurality of bores 1048 sized and configured to guide a wire or pin toward a bone segment. The ring wall 1036 also includes a number of grooves 1052 that extend into the ring wall 1036 and are spaced apart around the circumference. These grooves 1052 permit use to selectively cut portions of the ring wall 1036 based on the specific anatomy. In this regard, the shape and size of the curved member 1010 can be customized by the user. Thus, when in position, where the curved member 1010 has been cut, the curved member 1010 may extend only partially around the alignment axis 1024.

Another embodiment of a surgical tool 1100 shown in FIGS. 82-85 includes an elongated body 1114 with a first leg 1108, a second leg 1112, and a brace 1115 that connects the first leg 11008 to the second leg 1112. Like embodiments described above, the entirety of the brace 1115 is spaced apart and does not intersect the alignment axis 1124. In the embodiment shown, the first positioning element 1110 is a cone-shaped member coupled to the first leg 1108 of the elongated body 1114, the second positioning element 1120 is coupled to the second leg 1112 and includes a body 1128 with a channel 1132 that extends therethrough. Furthermore, the alignment axis 1124 passes through a center of the cone-shaped member 1110 and second positioning element 1120.

The cone-shaped member 1110 includes an outer wall 1136 that extends around the alignment axis. The outer wall 1136 includes an outer surface 1140, and inner surface 1144 opposite the outer surface 1140 and that faces the alignment axis 1124, the inner surface 1144 defining a substantial opening sized to receive a digit therethrough. In this manner, the outer wall 1136 can be placed over a toe or other digit. The outer wall 1136 also includes one or more grooves 1152 that extend through the outer wall 1136 and are spaced apart around the circumference. These grooves 1152 permit use to selectively cut portions of the outer wall 1136 based on the specific anatomy. In this regard, the shape and size of the cone-shaped member 1110 can be customized by the user. Thus, when in position, where the cone-shaped member 1110 has been cut, the cone-shaped member 1110 may extend only partially around the alignment axis 1124.

The embodiments described herein may be used in a method for fixing two or more bone segments in place. For example, the method generally includes forming a minimally invasive incision proximate a joint of a digit. Next, a user may insert a preparation tool into the incision toward the joint until a flange member of the preparation tool abuts a surface of the tissue proximate the joint. Using the preparation tool, the user may prepare bone surfaces at the joint with a cutting element of the preparation tool, such a burring tool. The preparation tool can then be removed. Next, a user may drill a target hole in a first bone segment at the joint with a drill. Once the target hole is formed, the first bone anchor may be implanted therein until the head of the bone anchor is positioned at the surface of the first bone segment and the shaft is anchored inside the first bone segment. Generally, the head will substantially flush with the bone surface in which it is implanted.

The first positioning element is positioned in the head of the implanted first bone anchor such that a second positioning element is aligned with a tip of the digit, to toe for example. At this point, the user can adjust the first positioning element in the head of the first bone anchor until alignment of the surgical tool and the first bone anchor is attained. Next, for example, a K-wire may be inserted in the second channel of the second positioning element, the tissue positioned between the first positioning element and the second positioning element, and first channel in the first positioning element.

The surgical tool is removed. The second bone anchor is then implanted over the K-wire until a distal end of the second bone anchor engages with at least the head of the first bone anchor. In this example, the second bone anchor is cannulated such that the second bone anchor slides over the K-wire.

In another embodiment of the present disclosure, the method includes forming a minimally invasive incision proximate a joint of a digit. Next, a user may insert a preparation tool into the incision toward the joint until a flange member of the preparation tool abuts a surface of the tissue proximate the joint. Using the preparation tool, the user may prepare bone surfaces at the joint with a cutting element of the preparation tool, such a burring tool. The preparation tool can then be removed. Next, a user may drill a target hole in a first bone segment at the joint with a drill. Once the target hole is formed, the first bone anchor may be implanted therein until the head of the bone anchor is positioned at the surface of the first bone segment and the shaft is anchored inside the first bone segment. Generally, the head will substantially flush with the bone surface in which it is implanted.

In this embodiment, the first positioning element, which is a ring member, is placed at least partially around the skin surface of the digit. In some cases, the ring member needs to be modified. Here, the user can remove a portion of a ring element of the first positioning element to form a resized ring element. Then, the user can place the resized ring element in position at least partially around the skin surface of the digit.

In another variation, it may be desirable to fix the ring member in place. In such an example, the user can place one or more fixation wires through one or more bores of a ring element of the first positioning element into contact with the first bone segment or skin surface of the digit.

At this point the user can adjust the first positioning element until alignment of the second positioning element of the surgical tool and the first bone anchor is attained. The surgical tool is removed. The second bone anchor is then implanted over the K-wire until a distal end of the second bone anchor engages with at least the head of the first bone anchor. In this example, the second bone anchor is cannulated such that the second bone anchor slides over the K-wire.

Wherever possible, the same or like reference numbers are used throughout the drawings to refer to the same or like features. It should be noted that the drawings are in simplified schematic form and are not drawn to precise scale. Certain terminology used in the description is for convenience only and is not limiting. Directional terms such as top, bottom, left, right, above, below and diagonal, are used with respect to the accompanying drawings. The term "distal" shall mean away from the center of a body. The term "proximal" shall mean closer towards the center of a body and/or away from the "distal" end. The words "inwardly" and "outwardly" refer to directions toward and away from, respectively, the geometric center of the identified element and designated parts thereof. Such directional terms used in conjunction with the following description of the drawings should not be construed to limit the scope of the present disclosure in any manner not explicitly set forth. Additionally, the term "a," as used in the specification, means "at least one." The terminology includes the words above specifically mentioned, derivatives thereof, and words of similar import.

"Substantially" as used herein shall mean considerable in extent, largely but not wholly that which is specified, or an appropriate variation therefrom as is acceptable within the field of art. "Exemplary" as used herein shall mean serving as an example.

Furthermore, the described features, advantages and characteristics of exemplary embodiments may be combined in any suitable manner in one or more embodiments. One skilled in the art will recognize, in light of the description herein, that the exemplary embodiments can be practiced without one or more of the specific features or advantages of a particular embodiment. In other instances, additional features and advantages may be recognized in certain embodiments that may not be present in all embodiments of the present disclosure.

While the disclosure is described herein, using a limited number of embodiments, these specific embodiments are not intended to limit the scope of the disclosure as otherwise described and claimed herein. The precise arrangement of various elements and order of the steps of articles and methods described herein are not to be considered limiting. For instance, although the steps of the methods are described with reference to sequential series of reference signs and progression of the blocks in the figures, the method can be implemented in an order as desired.

The invention claimed is:

1. A method, comprising:
forming a minimally invasive incision dorsal to a joint of a digit;
inserting a preparation tool into the incision toward the joint until a flange member of the preparation tool abuts a surface of tissue proximate the joint;
preparing bone surfaces at the joint with a cutting element of the preparation tool, the preparation tool including a shaft extending proximally relative to the flange member;
removing the preparation tool;
drilling a target hole in a first bone segment at the joint with a drill;
implanting a first bone anchor in the target hole until a head of the first bone anchor is positioned at the surface of the first bone segment and a shaft of the first bone anchor is anchored inside the first bone segment;

positioning a first positioning element of a surgical instrument in the head of the implanted first bone anchor such that a second positioning element is aligned with a tip of the digit;

adjusting the first positioning element in the head of the first bone anchor until alignment of the surgical tool and the first bone anchor is attained;

inserting a k-wire through a channel of the second positioning element, the tissue positioned between the first positioning element and the second positioning element, and a channel in the first positioning element; and implanting a second bone anchor over the K-wire until a distal end of the second bone anchor engages with at least the head of the first bone anchor, wherein the second bone anchor is cannulated such that the second bone anchor slides over the K-wire.

2. A method, comprising:

forming a minimally invasive incision dorsal to a joint of a digit;

inserting a preparation tool into the incision toward the joint until a flange member of the preparation tool abuts a surface of tissue proximate the joint;

preparing bone surfaces at the joint with a cutting element of the preparation tool, the preparation tool including a shaft extending proximally relative to the flange member;

removing the preparation tool;

drilling a target hole in a first bone segment at the joint with a drill;

positioning a first positioning element of a surgical instrument such that a second positioning element is aligned with a tip of the digit;

adjusting the first positioning element;

inserting a k-wire through a channel of the second positioning element, the tissue positioned between the first positioning element and the second positioning element, and a channel in the first positioning element; and implanting a bone anchor over the K-wire until a distal end of the bone anchor engages the bone, wherein the bone anchor is cannulated such that the bone anchor slides over the K-wire.

3. The method according to claim 2, further comprising removing a portion of a curved member of the first positioning element to form a resized ring element; and placing the resized ring element in position at least partially around a skin surface of the digit.

4. The method according to claim 2, further comprising placing one or more fixation wires through one or more apertures of a ring element of the first positioning element into contact with the first bone segment around a skin surface of the digit.

5. A method, comprising:

forming a minimally invasive incision proximate a joint of a digit;

inserting a preparation tool into the incision toward the joint until a flange member of the preparation tool abuts a surface of tissue proximate the joint;

preparing bone surfaces at the joint with a cutting element of the preparation tool, the preparation tool including a shaft extending proximally relative to the flange member;

removing the preparation tool;

drilling a target hole in a first bone segment at the joint with a drill;

implanting a first bone anchor in the target hole until a head of the first bone anchor is positioned at a surface of the first bone segment and a shaft of the first bone anchor is anchored inside the first bone segment;

placing a first positioning element at least partially around a skin surface of the digit;

adjusting the first positioning element until alignment of a second positioning element of the surgical tool and the first bone anchor is attained;

inserting a k-wire through a channel of the second positioning element, the tissue positioned between the first positioning element and the second positioning element, and a channel in the first positioning element; and implanting a second bone anchor over the K-wire until a distal end of the second bone anchor engages with at least the head of the first bone anchor, wherein the second bone anchor is cannulated such that the second bone anchor slides over the K-wire.

6. A method, comprising:

forming a minimally invasive incision proximate a joint of a digit;

inserting a preparation tool into the incision toward the joint until a flange member of the preparation tool abuts a surface of tissue proximate the joint;

preparing bone surfaces at the joint with a cutting element of the preparation tool, the preparation tool including a shaft extending proximally relative to the flange member;

removing the preparation tool;

drilling a target hole in a first bone segment at the joint with a drill;

placing a first positioning element at least partially around a skin surface of the digit;

adjusting the first positioning element to align a second positioning element;

inserting a k-wire through a channel of the second positioning element, the tissue positioned between the first positioning element and the second positioning element, and a channel in the first positioning element; and implanting a bone anchor over the K-wire until a distal end of the bone anchor engages the bone, wherein the bone anchor is cannulated such that the bone anchor slides over the K-wire.

* * * * *